(12) United States Patent
Weast et al.

(10) Patent No.: US 11,081,207 B2
(45) Date of Patent: *Aug. 3, 2021

(54) ENERGY EXPENDITURE

(71) Applicant: NIKE, Inc., Beaverton, OR (US)

(72) Inventors: Aaron B. Weast, Portland, OR (US);
Aaron K. Goodwin, Bend, OR (US);
James M. Mullin, Bend, OR (US);
John M. Schmitt, Bend, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/942,249

(22) Filed: Jul. 29, 2020

(65) Prior Publication Data
US 2020/0372968 A1 Nov. 26, 2020

Related U.S. Application Data

(63) Continuation of application No. 15/977,486, filed on May 11, 2018, now Pat. No. 10,734,094, which is a
(Continued)

(51) Int. Cl.
*G16B 5/00* (2019.01)
*G16B 99/00* (2019.01)
(Continued)

(52) U.S. Cl.
CPC ............... *G16B 5/00* (2019.02); *A61B 5/024* (2013.01); *A61B 5/4866* (2013.01);
(Continued)

(58) Field of Classification Search
CPC .... G16B 5/00; G09B 19/003; G09B 19/0038; G16H 20/30; G01P 15/00; G01C 22/006; G06F 17/00; A61B 5/024; A61B 5/4866
See application file for complete search history.

(56) References Cited

U.S. PATENT DOCUMENTS 5,788,655 A 8/1998 Yoshimura et al.
6,241,648 B1 6/2001 Uera et al.
(Continued)

FOREIGN PATENT DOCUMENTS

EP 1619475 A2 1/2006
GB 2447647 A 9/2008
(Continued)

OTHER PUBLICATIONS

Pontzer et al., Control and Function of Arm Swing in Human Walking and Running, 2009, The Journal of Experimental Biology 212, Published by The Company of Biologists, pp. 523-534 (Year: 2009).*

(Continued)

*Primary Examiner* — Toan M Le
(74) *Attorney, Agent, or Firm* — Banner & Witcoff, Ltd.

(57) ABSTRACT

Aspects relate to calculating energy expenditure values from an apparatus configured to be worn on an appendage of a user. Steps counts may be quantified, such as by detecting arm swings peaks and bounce peaks in motion data. A search range of acceleration frequencies related to an expected activity may be established. Frequencies of acceleration data within a search range may be analyzed to identify one or more peaks, such as a bounce peak and an arm swing peak. Novel systems and methods may determine whether to utilize the arm swing data, bounce data, and/or other data or portions of data to quantify steps. The number of peaks (and types of peaks) may be used to choose a step frequency and step magnitude. At least a portion of the motion data may be classified into an activity category based upon the quantification of steps.

20 Claims, 16 Drawing Sheets

Related U.S. Application Data continuation of application No. 15/657,820, filed on Jul. 24, 2017, now Pat. No. 9,996,660, which is a continuation of application No. 15/355,243, filed on Nov. 18, 2016, now Pat. No. 9,747,411, which is a continuation of application No. 13/744,103, filed on Jan. 17, 2013, now Pat. No. 9,529,966.

(60) Provisional application No. 61/588,647, filed on Jan. 19, 2012.

(51) Int. Cl.
*G09B 19/00* (2006.01)
*G16H 40/67* (2018.01)
*G06F 17/00* (2019.01)
*A61B 5/024* (2006.01)
*A61B 5/00* (2006.01)
*G01C 22/00* (2006.01)
*G01P 15/00* (2006.01)
*G16H 20/40* (2018.01)
*G16H 20/30* (2018.01)

(52) U.S. Cl.
CPC ............ *G01C 22/006* (2013.01); *G01P 15/00* (2013.01); *G06F 17/00* (2013.01); *G09B 19/003* (2013.01); *G09B 19/0038* (2013.01); *G16B 99/00* (2019.02); *G16H 20/30* (2018.01); *G16H 20/40* (2018.01); *G16H 40/67* (2018.01)

(56) References Cited

U.S. PATENT DOCUMENTS

| | | | |
|---|---|---|---|
| 6,513,532 | B2 | 2/2003 | Mault et al. |
| 7,212,943 | B2 | 5/2007 | Aoshima et al. |
| 7,805,149 | B2 | 9/2010 | Werner et al. |
| 8,562,489 | B2 | 10/2013 | Burton et al. |
| 9,529,966 | B2 | 12/2016 | Weast et al. |
| 9,747,411 | B2 | 8/2017 | Weast et al. |
| 9,996,660 | B2 * | 6/2018 | Weast ............... G16B 99/00 |
| 10,734,094 | B2 * | 8/2020 | Weast ............... G06F 19/3481 |
| 2005/0107216 | A1 | 5/2005 | Lee et al. |
| 2006/0020177 | A1 | 1/2006 | Seo et al. |
| 2006/0136173 | A1 | 6/2006 | Case et al. |
| 2008/0200312 | A1 | 8/2008 | Tagliabue |
| 2008/0214360 | A1 | 9/2008 | Stirling et al. |
| 2008/0250337 | A1 | 10/2008 | Lemmela et al. |
| 2008/0288200 | A1 | 11/2008 | Noble |
| 2009/0258710 | A1 | 10/2009 | Quatrochi et al. |
| 2009/0262088 | A1 | 10/2009 | Moll-Carrillo et al. |
| 2010/0198087 | A1 | 8/2010 | Takahashi et al. |
| 2010/1098626 | | 8/2010 | Cho et al. |
| 2010/0273610 | A1 | 10/2010 | Johnson |
| 2010/0279167 | A1 | 11/2010 | Watson et al. |
| 2010/0287178 | A1 | 11/2010 | Lambert et al. |
| 2010/0305480 | A1 | 12/2010 | Fu et al. |
| 2010/0331145 | A1 | 12/2010 | Lakovic et al. |
| 2011/0003665 | A1 | 1/2011 | Burton et al. |
| 2011/0007468 | A1 | 1/2011 | Burton et al. |
| 2011/0032105 | A1 | 2/2011 | Hoffman et al. |
| 2011/0082636 | A1 | 4/2011 | Barker et al. |
| 2011/0098928 | A1 | 4/2011 | Hoffman et al. |
| 2011/0196603 | A1 | 8/2011 | Graham et al. |
| 2012/0100850 | A1 | 4/2012 | Huang |
| 2012/0116550 | A1 | 5/2012 | Hoffman et al. |
| 2012/0253485 | A1 | 10/2012 | Weast et al. |

FOREIGN PATENT DOCUMENTS

| | | |
|---|---|---|
| JP | H11042220 A | 2/1999 |
| JP | 200278697 A | 3/2002 |
| JP | 2004097649 A | 4/2004 |
| JP | 2004113821 A | 4/2004 |
| JP | 2007252914 A | 10/2007 |
| JP | 2008076210 A | 4/2008 |
| JP | 2008084271 A | 4/2008 |
| JP | 2008131425 A | 6/2008 |
| JP | 2008246179 A | 10/2008 |
| JP | 2009131482 A | 6/2009 |
| JP | 2010017525 A | 1/2010 |
| JP | 2010274119 A | 12/2010 |
| JP | 2014048239 A | 3/2014 |
| KR | 20080051665 A | 6/2008 |
| WO | 2009065637 A1 | 5/2009 |

OTHER PUBLICATIONS

Giovanni A. Cavagna, Symmetry and Asymmetry in Bouncing Gaits, Symmetry 2010, 2, pp. 1270-1321 (Year: 2010).*

Mar. 27, 2014—(WO) ISR and WO—App. No. PCT/US13/44214.

Mokey. http://www.digitaitrends.eom/watch-reviews/nike-pius-sportwatch-gps-review/2/. Digitaitrends.com. Archive.org: Apr. 25, 2011. Accessed Jan. 16, 2014.

Ross, www.runtheline.com/1552/nike-sportswatch-gps-running-watch-review#. Runtheline.com. Archive.org: May, 19, 2011. Accessed Jan. 14, 2014.

Jul. 15, 2013—(WO) ISR and WO—App. No. PCT\US2013\021976.

Andre et al., The Development of the SenseWear Armband, a Revolutionary Energy Assessment Device to Assess Physical Activity and Lifestyle, 2006, Body Media, Inc., pp. 1-19.

Doke, et al., Mechanics and Energetics of Swinging the Human Leg, 2005. The Journal of Experimental Biology 208, pp. 430-445.

Dean et al., Energetic Costs of Producing Muscle Work and Force in a Cyclical Human Bouncing Task, 2011, J. Appl. Physiol. 110, pp. 873-880.

Andre et al., The Development of the SenseWear armband, a Revolutionary Energy Assessment Device to Assess Physical Activity and Lifestyle, 2006 BodyMedia, Inc.

* cited by examiner

ENERGY EXPENDITURE

CROSS REFERENCE TO RELATED APPLICATIONS

This application is a continuation of U.S. patent application Ser. No. 15/977,486, filed May 11, 2018, issued as U.S. Pat. No. 10,734,094, which is a continuation of Ser. No. 15/657,820, filed Jul. 24, 2017, issued as U.S. Pat. No. 9,996,660, which is a continuation of U.S. patent application Ser. No. 15/355,243, filed Nov. 18, 2016, issued as U.S. Pat. No. 9,747,411, which is a continuation of U.S. patent application Ser. No. 13/744,103, filed Jan. 17, 2013, issued as U.S. Pat. No. 9,529,966, which claims the benefit of, and priority to, U.S. Provisional Patent Application No. 61/588,647 filed Jan. 19, 2012. The content of each of these applications is expressly incorporated herein by reference in its entirety for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interest are ignored. This may further decrease a user's interest in participating in athletic activities or using athletic activity services and systems.

Many existing services and devices fail to provide accurate assessment of the user's energy expenditure, such as caloric burn, during physical activity. Therefore, users are unaware of the benefits that certain activities, which may include daily routines that are often not thought of as being a "workout", are to their health. Existing devices for allowing users to monitor their energy expenditure often suffer from one or more deficiencies, including: cumbersome collection systems, inaccurate measurements that are beyond an acceptable threshold, unacceptable latency in reporting the values, erroneous classification of activities based upon detected motions of the user, failure to account for deviations between different users (for example, proper classification for individuals who do not "bounce" during walking and/or running to the same extent as an "average" individual), improperly including repetitive behavior as being classified as a specific activity, such as for example, running and/or walking, relatively high power consumption, and/or a combination of these or other deficiencies.

Therefore, improved systems and methods to address at least one or more of these shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of this disclosure relate to calculating energy expenditure values. One or more devices may use an accelerometer and/or other sensors to monitor physical activities of a user. In one embodiment, an apparatus is configured to be worn on an appendage of a user and may be used to collect and process motion data. The apparatus may include a processor, at least one sensor configured to capture motion data of the user, and a memory comprising computer-executable instructions that when executed by the processor, collects and analyzes the motion data. The motion data may be utilized to determine an energy expenditure value. The apparatus may be configured to capture motion data of the user with the sensor while being worn on an appendage of the user. It may be configured to be worn on the arm, such as but not limited to being located by a wrist, of the user. Certain implementations may be entirely performed on a single apparatus.

In certain embodiments, the only sensor data utilized to collect the motion data is collected (or derived) from the apparatus worn by the user. In further embodiments, at least one of the following is performed entirely on the device worn by the user: quantification of steps, determining which data used to quantify and/or detect steps, organizing the data into activity categories, and/or determining an energy expenditure value. In certain embodiments, the apparatus already contains information, such as a metabolic equivalence value or data or information utilized in the calculations on a computer-readable medium located on the apparatus. Thus, no external information is required during the calculations.

Certain implementations may quantify steps taken by the user based upon the motion data, such as by detecting arm swings peaks and bounce peaks in the motion data. The quantification may be done based entirely upon data collected from a single device worn on the user's arm, such as for example, proximate to the wrist. In one embodiment, motion data is obtained from an accelerometer. Accelerometer magnitude vectors may be obtained for a time frame and values, such as an average value from magnitude vectors for the time frame may be calculated. The average value (or any other value) may be utilized to determine whether magnitude vectors for the time frame meet an acceleration threshold to qualify for use in calculating step counts for the respective time frame. Acceleration data meeting a threshold may be placed in an analysis buffer. A search range of acceleration frequencies related to an expected activity may be established. Frequencies of the acceleration data within the search range may be analyzed in certain implementations to identify one or more peaks, such as a bounce peak and an arm swing peak. In one embodiment, a first frequency peak may be identified as an arm swing peak if it is within an estimated arm swing range and further meets an arm swing peak threshold. Similarly, a second frequency peak may be determined to be a bounce peak if it is within an estimated bounce range and further meets a bounce peak threshold.

Novel systems and methods may determine whether to utilize the arm swing data, bounce data, and/or other data or portions of data to quantify steps. The number of peaks, such as arm swing peaks and/or bounce peaks may be used to determine which data to utilize. In one embodiment, systems and methods may use the number of peaks (and types of peaks) to choose a step frequency and step magnitude for quantifying steps. In still further embodiments, at least a portion of the motion data may be classified into an activity category based upon the quantification of steps.

In one embodiment, the sensor signals (such as accelerometer frequencies) and the calculations based upon sensor signals (e.g., a quantity of steps) may be utilized in the classification of an activity category, such as either walking or running, for example. In certain embodiments, if data cannot be categorized as being within a first category (e.g., walking) or group of categories (e.g., walking and running), a first method may analyze collected data. For example, in one embodiment, if detected parameters cannot be classified, then a Euclidean norm equation may be utilized for further analysis. In one embodiment, an average magnitude vector norm (square root of the sum of the squares) of obtained values may be utilized. In yet another embodiment, a different method may analyze at least a portion of the data following classification within a first category or groups of categories. In one embodiment, a step algorithm, such as those disclosed herein, may be utilized. Classified and unclassified data may be utilized to calculate an energy expenditure value.

A memory may include instructions that when executed by the processor of the apparatus, combine the energy expenditure value for the first time period with an energy expenditure value from a second time period to determine an accumulated energy expenditure value. An apparatus may include a display configured to be observable by the user while the apparatus is being worn by that user. The device may be configured to display the accumulated energy expenditure value on the display. The displaying of energy expenditure values on a device may be responsive to receiving a user input from a user input device located on the device. The display may include a length of light-emitting structures, such as LEDs that are configured to provide an indication of the energy expenditure. In one embodiment, the displayed expenditure may be in relation to a goal, such as a goal set by the user.

In some embodiments, the present invention can be partially or wholly implemented on a computer-readable medium, for example, by storing computer-executable instructions or modules, or by utilizing computer-readable data structures.

Of course, the methods and systems of the above-referenced embodiments may also include other additional elements, steps, computer-executable instructions, or computer-readable data structures.

The details of these and other embodiments of the present invention are set forth in the accompanying drawings and the description below. Other features and advantages of the invention will be apparent from the description and drawings, and from the claims.

BRIEF DESCRIPTION OF THE DRAWINGS

The present disclosure is illustrated by way of example and not limited in the accompanying figures in which like reference numerals indicate similar elements and in which:

FIGS. 1A-B illustrate an example of a system that may be used to collect and analyze motion data, wherein FIG. 1A illustrates an example network configured to collect and analyze athletic activity, and FIG. 1B illustrates an example computing device in accordance with example embodiments;

FIG. 4A is a flowchart that may be used to collect and analyze motion data in accordance with one embodiment and FIG. 4B is a flowchart that may be used to identify data ranges for detecting steps or other physical activities of a user in accordance with one embodiment;

FIG. 7A shows a graph plotting FFT power against frequency data that includes data within an arm swing range and data within a bounce range; and FIG. 7B shows the same graph with a threshold utilized to determine if peaks within the bounce range meet a criterion;

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

I. Example Personal Training System

A. Illustrative Computing Devices

Figure 1A:
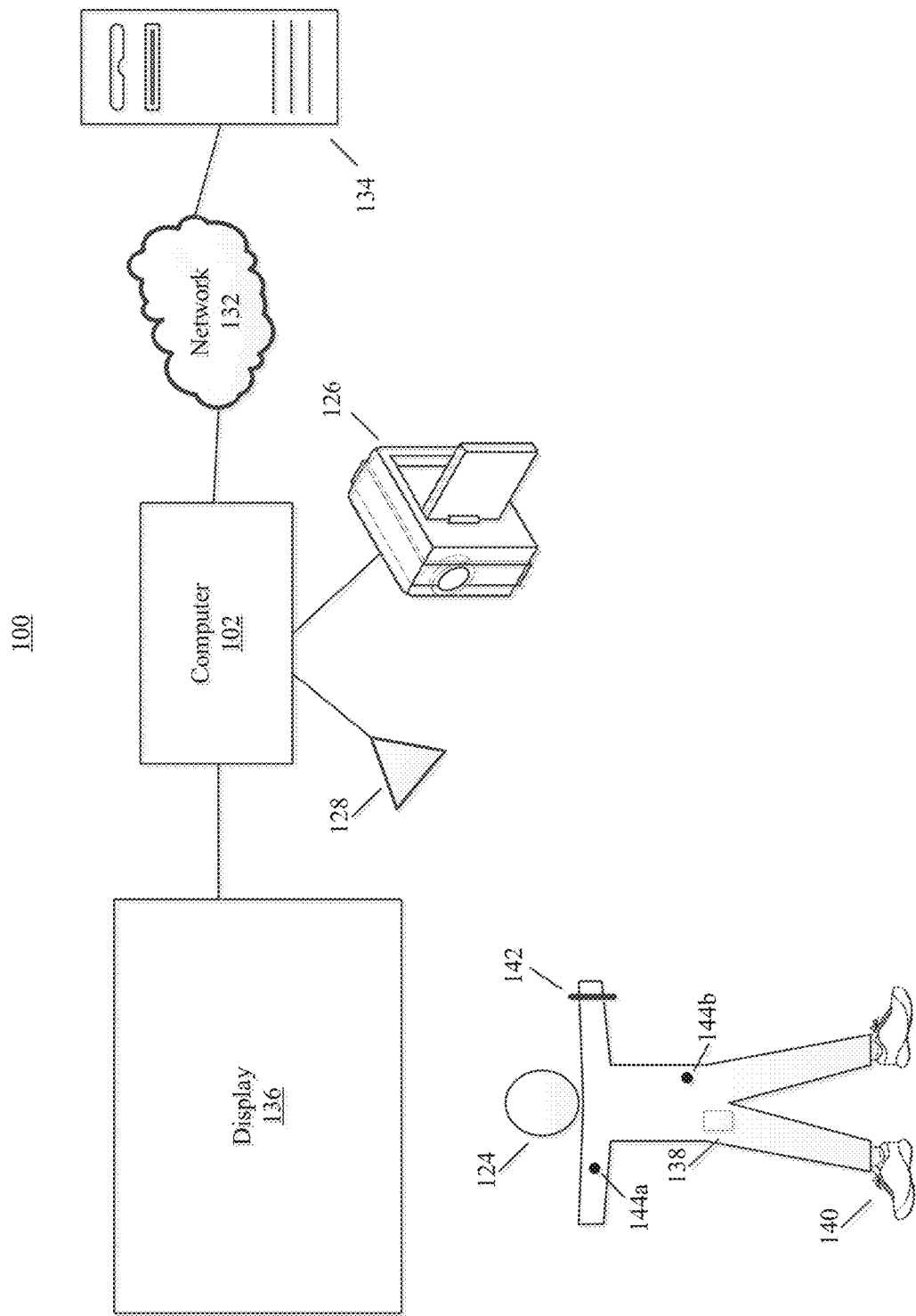

FIG. 1A illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server(s), and/or any other desired computing device. In certain configurations, computer 102 may comprise a gaming console, such as for example, a Microsoft® XBOX, Sony® PlayStation, and/or a Nintendo® Wii gaming consoles. Those skilled in the art will appreciate that these are merely example consoles for descriptive purposes and this disclosure is not limited to any console or device.

Figure 1B:
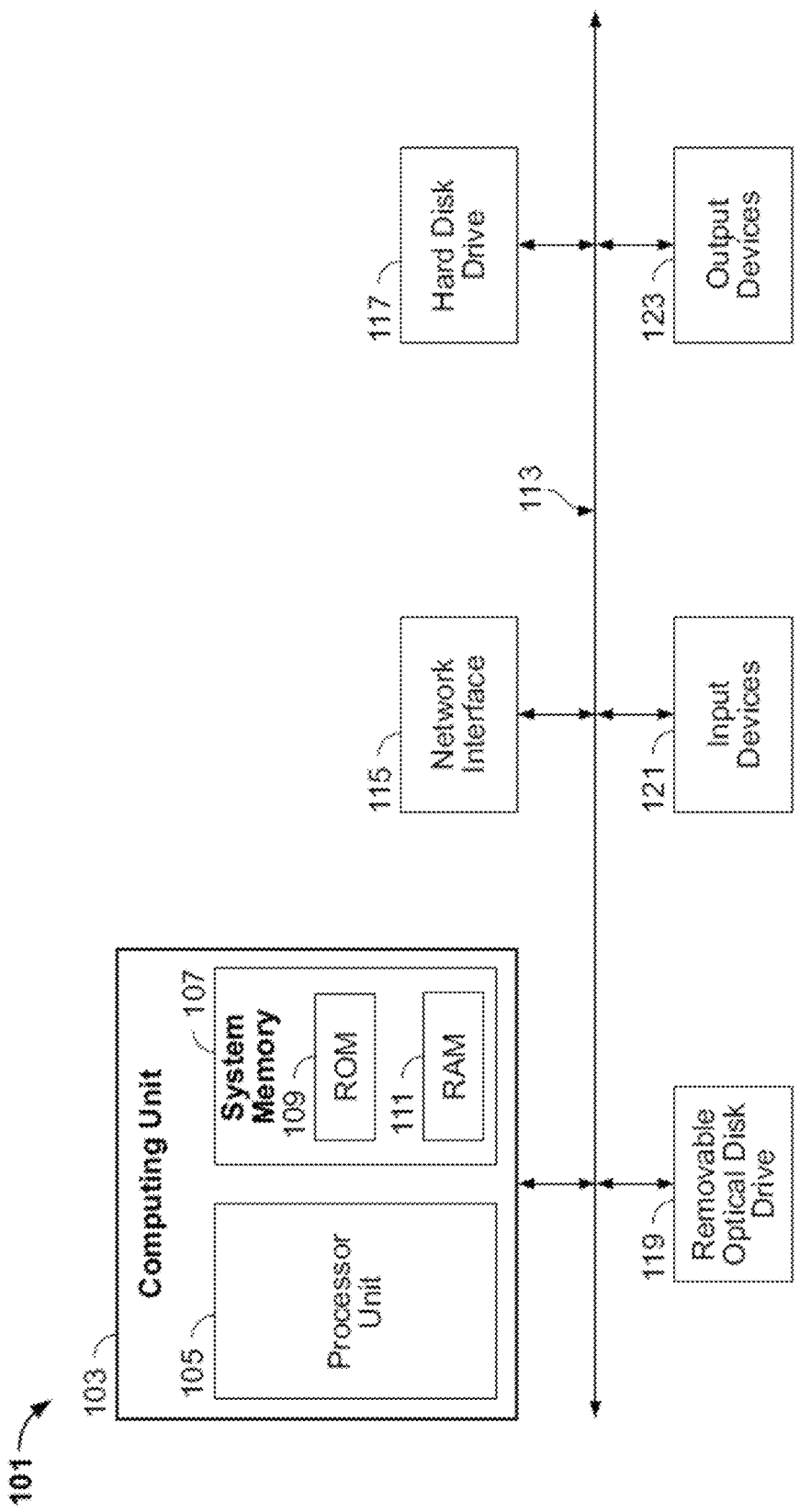

Turning briefly to FIG. 1B, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card. The processing unit 106 and the system memory 108 also may be directly or indirectly connected to one or more input devices 120 and one or more output devices 122. The output devices 122 may include, for example, a display device 136, television, printer, stereo, or speakers. In some embodiments one or more display devices may be incorporated into eyewear. The display devices incorporated into eyewear may provide feedback to users. Eyewear incorporating one or more display devices also provides for a portable display system. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user 124, shown in FIG. 1A.

Looking again to FIG. 1A, image-capturing device 126 and/or sensor 128 may be utilized in detecting and/or measuring athletic movements of user 124. In one embodiment, data obtained from image-capturing device 126 or sensor 128 may directly detect athletic movements, such that the data obtained from image-capturing device 126 or sensor 128 is directly correlated to a motion parameter. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C, entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

B. Illustrative Network

Computer 102, computing unit 104, and/or any other electronic devices may be directly or indirectly connected to one or more network interfaces, such as example interface 130 (shown in FIG. 1B) for communicating with a network, such as network 132. In the example of FIG. 1B, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topology(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102. Indeed, system 100 may include more than one instance of each component (e.g., more than one computer 102, more than one display 136, etc.).

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1A. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

C. Illustrative Sensors

Computer 102 and/or other devices may comprise one or more sensors 126, 128 configured to detect and/or monitor at least one fitness parameter of a user 124. Sensors 126 and/or 128 may include, but are not limited to: an accelerometer, a gyroscope, a location-determining device (e.g., GPS), light sensor, temperature sensor (including ambient temperature and/or body temperature), sleep pattern sensors, heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oreg. Although image capturing device 126 and sensor 128 and display 136 are shown in direct (wirelessly or wired) communication with computer 102, those skilled in the art will appreciate that any may directly communicate (wirelessly or wired) with network 132.

1. Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144*a*-*b*. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub. No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Devices 138-144 may communicate with each other, either directly or through a network, such as network 132. Communication between one or more of devices 138-144 may take place via computer 102. For example, two or more of devices 138-144 may be peripherals operatively connected to bus 114 of computer 102. In yet another embodiment, a first device, such as device 138 may communicate with a first computer, such as computer 102 as well as another device, such as device 142; however, device 142 may not be configured to connect to computer 102 but may communicate with device 138. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 1B may be included in the server 134, other computers, apparatuses, etc.

2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

i. Shoe-Mounted Device

In certain embodiments, sensory device 140 may comprise footwear which may include one or more sensors, including but not limited to: an accelerometer, location-sensing components, such as GPS, and/or a force sensor system. FIG. 2A illustrates one example embodiment of a sensor system 202. In certain embodiments, system 202 may include a sensor assembly 204. Assembly 204 may comprise one or more sensors, such as for example, an accelerometer, location-determining components, and/or force sensors. In the illustrated embodiment, assembly 204 incorporates a plurality of sensors, which may include force-sensitive resistor (FSR) sensors 206. In yet other embodiments, other sensor(s) may be utilized. Port 208 may be positioned within a sole structure 209 of a shoe. Port 208 may optionally be provided to be in communication with an electronic module 210 (which may be in a housing 211) and a plurality of leads 212 connecting the FSR sensors 206 to the port 208. Module 210 may be contained within a well or cavity in a sole structure of a shoe. The port 208 and the module 210 include complementary interfaces 214, 216 for connection and communication.

In certain embodiments, at least one force-sensitive resistor 206 shown in FIG. 2A may contain first and second electrodes or electrical contacts 218, 220 and a force-sensitive resistive material 222 disposed between the electrodes 218, 220 to electrically connect the electrodes 218, 220 together. When pressure is applied to the force-sensitive material 222, the resistivity and/or conductivity of the force-sensitive material 222 changes, which changes the electrical potential between the electrodes 218, 220. The change in resistance can be detected by the sensor system 202 to detect the force applied on the sensor 216. The force-sensitive resistive material 222 may change its resistance under pressure in a variety of ways. For example, the force-sensitive material 222 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 222 may change the resistance by changing the degree of surface-to-surface contact. This can be achieved in several ways, such as by using microprojections on the surface that raise the surface resistance in an uncompressed condition, where the surface resistance decreases when the microprojections are compressed, or by using a flexible electrode that can be deformed to create increased surface-to-surface contact with another electrode. This surface resistance may be the resistance between the material 222 and the electrode 218, 220 222 and/or the surface resistance between a conducting layer (e.g., carbon/graphite) and a force-sensitive layer (e.g., a semiconductor) of a multi-layer material 222. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 222, as defined herein, may be or include a doped or non-doped semiconducting material.

The electrodes 218, 220 of the FSR sensor 216 can be formed of any conductive material, including metals, carbon/graphite fibers or composites, other conductive composites, conductive polymers or polymers containing a conductive material, conductive ceramics, doped semiconductors, or any other conductive material. The leads 212 can be connected to the electrodes 218, 220 by any suitable method, including welding, soldering, brazing, adhesively joining, fasteners, or any other integral or non-integral joining method. Alternately, the electrode 218, 220 and associated lead 212 may be formed of a single piece of the same material.

ii. Wrist-Worn Device

Figure 2B:
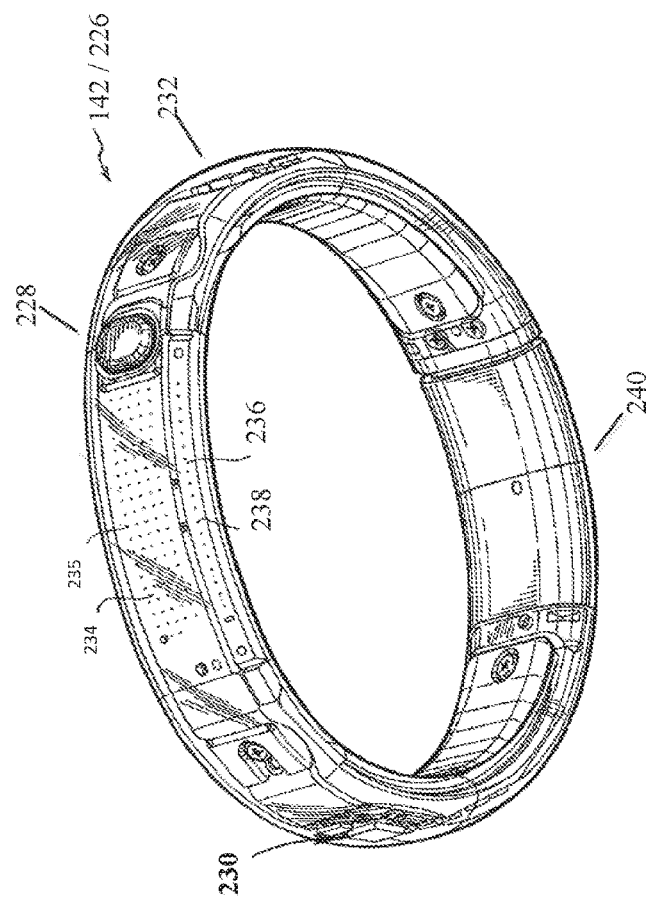
FIGS. 2A and 2B illustrate example sensor assemblies that may be worn by a user in accordance with example embodiments.
Figure 2A:
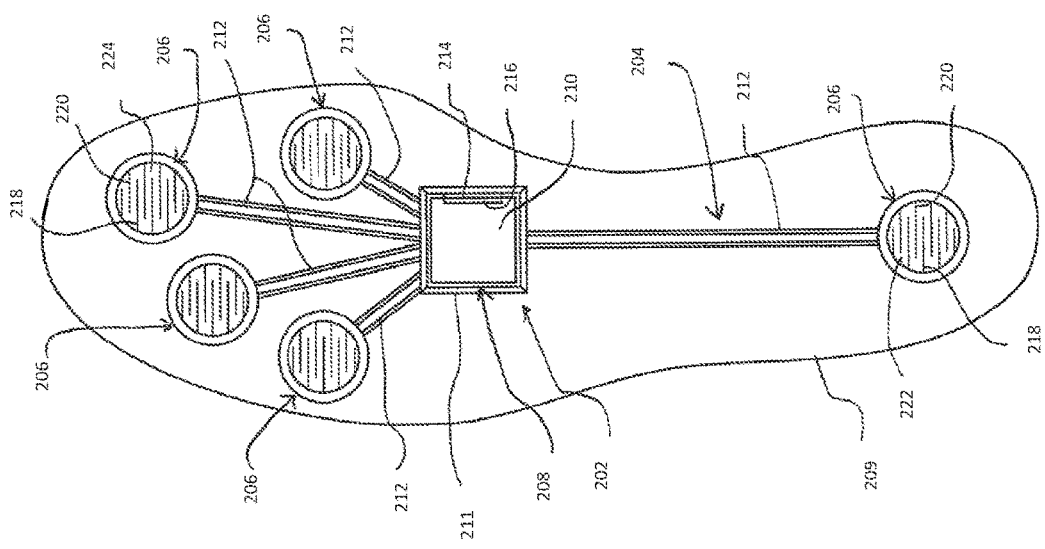

As shown in FIG. 2B, device 226 (which may resemble or be sensory device 142 shown in FIG. 1A) may be configured to be worn by user 124, such as around a wrist, arm, ankle or the like. Device 226 may monitor athletic movements of a user, including all-day activity of user 124. In this regard, device assembly 226 may detect athletic movement during user's 124 interactions with computer 102 and/or operate independently of computer 102. For example, in one embodiment, device 226 may be an-all day activity monitor that measures activity regardless of the user's proximity or interactions with computer 102. Device 226 may communicate directly with network 132 and/or other devices, such as devices 138 and/or 140. In other embodiments, athletic data obtained from device 226 may be utilized in determinations conducted by computer 102, such as determinations relating to which exercise programs are presented to user 124. In one embodiment, device 226 may also wirelessly interact with a mobile device, such as device 138 associated with user 124 or a remote website such as a site dedicated to fitness or health related subject matter. At some predetermined time, the user may wish to transfer data from the device 226 to another location.

As shown in FIG. 2B, device 226 may include an input mechanism, such as a depressible input button 228 assist in operation of the device 226. The input button 228 may be operably connected to a controller 230 and/or any other electronic components, such as one or more of the elements discussed in relation to computer 102 shown in FIG. 1B. Controller 230 may be embedded or otherwise part of housing 232. Housing 232 may be formed of one or more materials, including elastomeric components and comprise one or more displays, such as display 234. The display may be considered an illuminable portion of the device 226. The display 234 may include a series of individual lighting elements or light members such as LED lights 234 in an exemplary embodiment. The LED lights may be formed in an array and operably connected to the controller 230. Device 226 may include an indicator system 236, which may also be considered a portion or component of the overall display 234. It is understood that the indicator system 236 can operate and illuminate in conjunction with the display 234 (which may have pixel member 235) or completely separate from the display 234. The indicator system 236 may also include a plurality of additional lighting elements or light members 238, which may also take the form of LED lights in an exemplary embodiment. In certain embodiments, indicator system may provide a visual indication of goals, such as by illuminating a portion of lighting members 238 to represent accomplishment towards one or more goals.

A fastening mechanism 240 can be unlatched wherein the device 226 can be positioned around a wrist of the user 124 and the fastening mechanism 240 can be subsequently placed in a latched position. The user can wear the device 226 at all times if desired. In one embodiment, fastening mechanism 240 may comprise an interface, including but not limited to a USB port, for operative interaction with computer 102 and/or devices 138, 140.

In certain embodiments, device 226 may comprise a sensor assembly (not shown in FIG. 2B). The sensor assembly may comprise a plurality of different sensors. In an example embodiment, the sensor assembly may comprise or permit operative connection to an accelerometer (including in the form of a multi-axis accelerometer), heart rate sensor, location-determining sensor, such as a GPS sensor, and/or other sensors. Detected movements or parameters from device's 142 sensor(s), may include (or be used to form) a variety of different parameters, metrics or physiological characteristics including but not limited to speed, distance, steps taken, calories, heart rate, sweat detection, effort, oxygen consumed, and/or oxygen kinetics. Such parameters may also be expressed in terms of activity points or currency earned by the user based on the activity of the user.

II. Energy Expenditure

Figure 3:
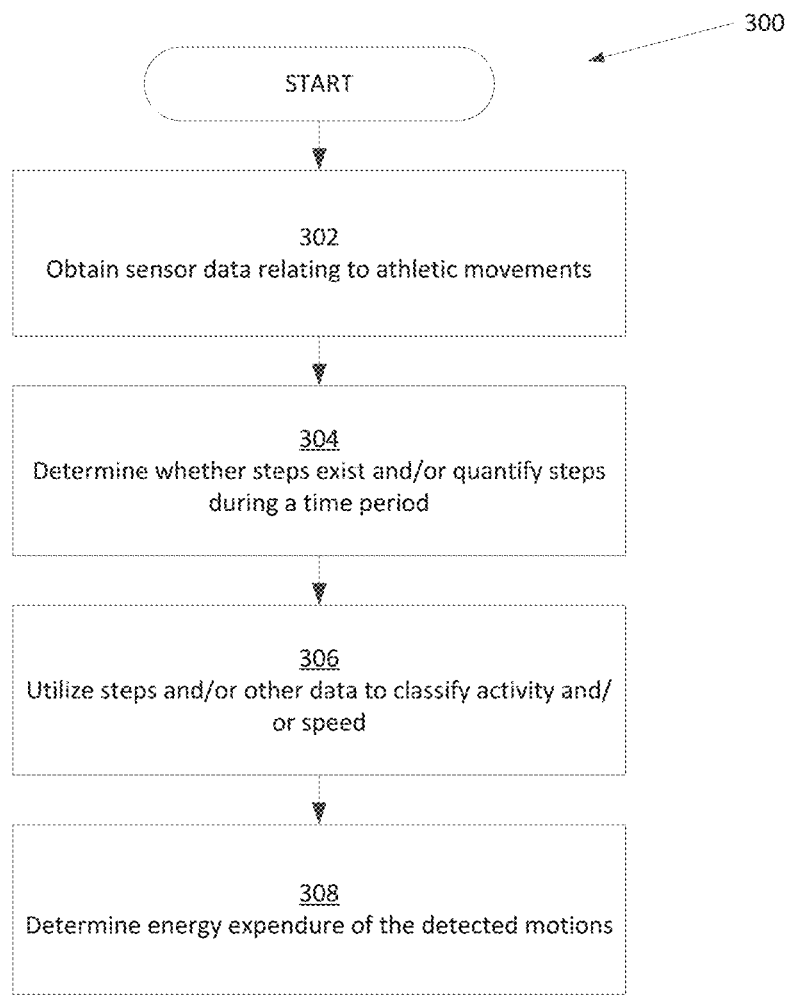
FIG. 3 shows an example flowchart that may be utilized to quantify energy expenditure values in accordance with one embodiment.

Certain aspects of this disclosure relate to determining energy expenditure, such as with one or more of the sensors of system 100. In one embodiment, sensors solely located on a device configured to be worn by a user, such as a wrist-worn device, may be utilized to detected motion parameters. Data from sensors on such as device may be used without the assistance of other sensors in one or more determinations relating to classifying activity and/or determine energy expenditure. The activity may include athletic and/or other physical activity of user 124. FIG. 3 is a flowchart 300 showing an illustrative process that may be utilized to classify activity and/or calculate energy expenditure values of an individual in accordance with one embodiment. FIG. 3 is provided as an overview of exemplary embodiments that may comprise a plurality of sub-elements. In this regard, the remaining figures (and related disclosure) following FIG. 3 may optionally be used in conjunction with FIG. 3 and/or each other to provide a full system that obtains sensor data and provides energy expenditure values. In accordance with other embodiments, one or more different systems and methods discussed below may be used alone or in combination with only a portion of other disclosed systems and methods to provide one or more of: step counts, activity classifications, and energy expenditures, among others. Various embodiments of step quantification systems and methods may relate to a low power, high fidelity, integer-based step counter using a multi-tier technique. These and other embodiments are described below.

In accordance with a first embodiment, a plurality of samples from one or more sensors (e.g., sensors 126, 128, and/or 138-142) may be obtained during a first time period (see, e.g., block 302). In certain configurations, at least one sensor (e.g. sensor 142) may comprise an accelerometer. The accelerometer may be a multi-axis accelerometer. In another embodiment, however, a plurality of accelerometers may be utilized. Other non-accelerometer based sensors are also within the scope of this disclosure, either in combination with an accelerometer or individually. Indeed, any sensor(s) configurable to detect or measure athletic movement and/or physiologic properties are within the scope of this disclosure. In this regard, data may be obtained and/or derived from a plurality of sensors, including for example, location sensors (e.g., GPS), heart rate sensors, force sensors, gyroscope, etc. In one embodiment, various systems and methods are implemented, at least partially, on a portable device. In certain embodiments, the portable device may be a wrist-worn device (see, e.g., sensor 142). In one embodiment, sensor data from a device configured to be worn on a human appendage (e.g., wrist, arm, neck, ankles, leg, etc.) may be utilized without other sensor data. Motion data, such as measured through an accelerometer and/or other sensors, may be loaded into a multi-segment threshold based acceleration buffer.

Further aspects relate to detecting and/or measuring an athletic parameter, such as for example, a quantity of steps taken by a user, such as user 124. One or more system or methods may utilize various portions of the data (such as in an acceleration buffer comprising accelerometer data) to determine if detected parameters are indicative of a specific action or activity. In one embodiment, a quantity of steps may be detected during a predefined period of time (See, e.g., block 304). Examples of different systems and methods that may be utilized to quantify the number of steps taken by the user during a time period (or even determine whether steps exist in the sensor data) are provided in context of FIGS. 4-8, and will be discussed below. In one embodiment, step data and/or other motion data may be utilized in the classification of activity, such as either walking or running, for example (see, e.g., block 306). In certain embodiments, if data cannot be categorized as being within a first category (e.g., walking) or group of categories (e.g., walking and running), a first method may analyze collected data. For example, in one embodiment, if detected parameters cannot be classified, then a Euclidean norm equation may be utilized for further analysis. In one embodiment, an average magnitude vector norm (square root of the sum of the squares) of obtained values may be utilized. In yet another embodiment, a different method may analyze at least a portion of the data following classification within a first category or groups of categories. In one embodiment, a step algorithm, such as those disclosed herein, may be utilized. This disclosure further provides some examples of classification processes that may be implemented (see, e.g., FIG. 9).

Figure 10:
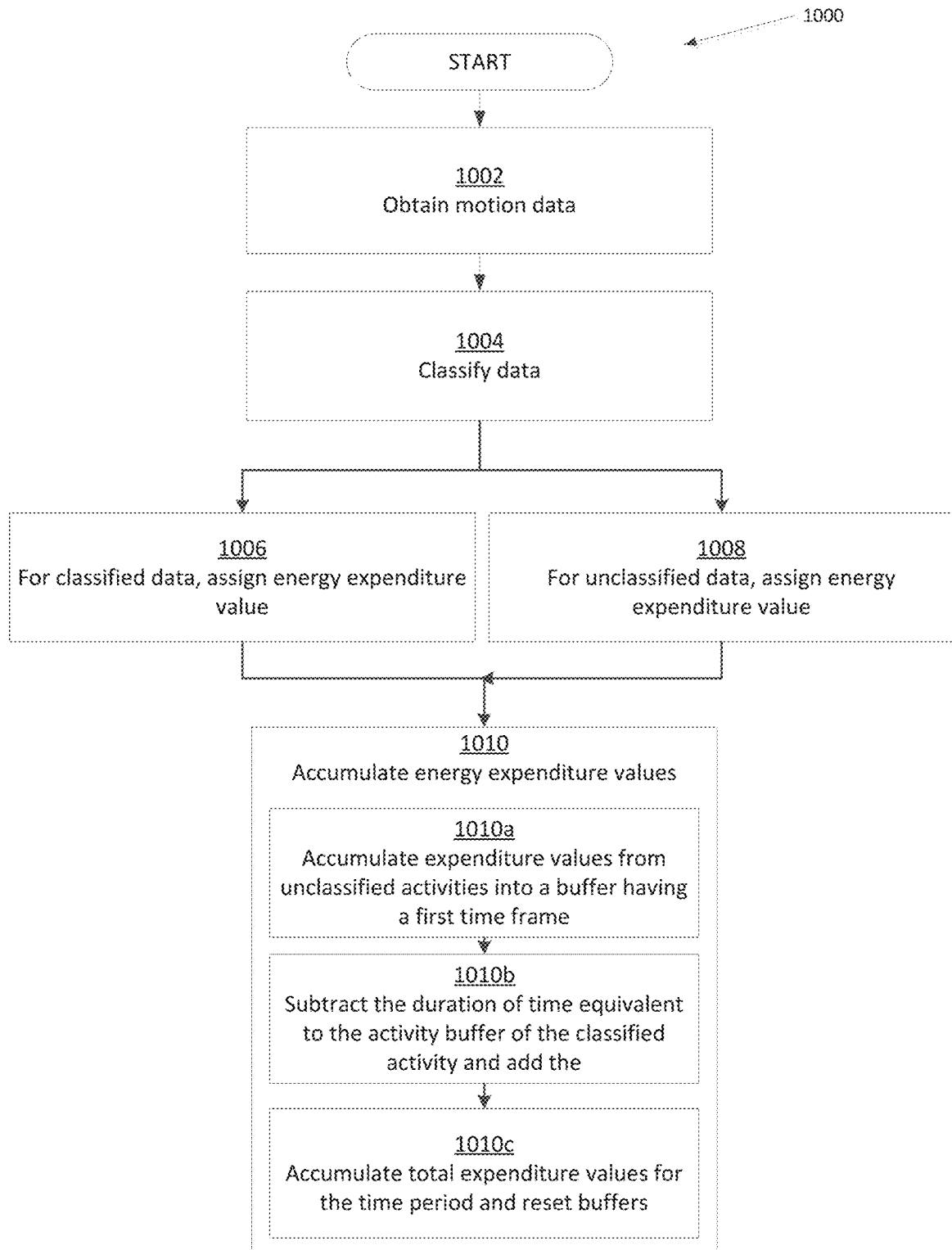
FIG. 10 shows an example flowchart that may be implemented to determine energy expenditure values in accordance with one embodiment.
Figure 11:
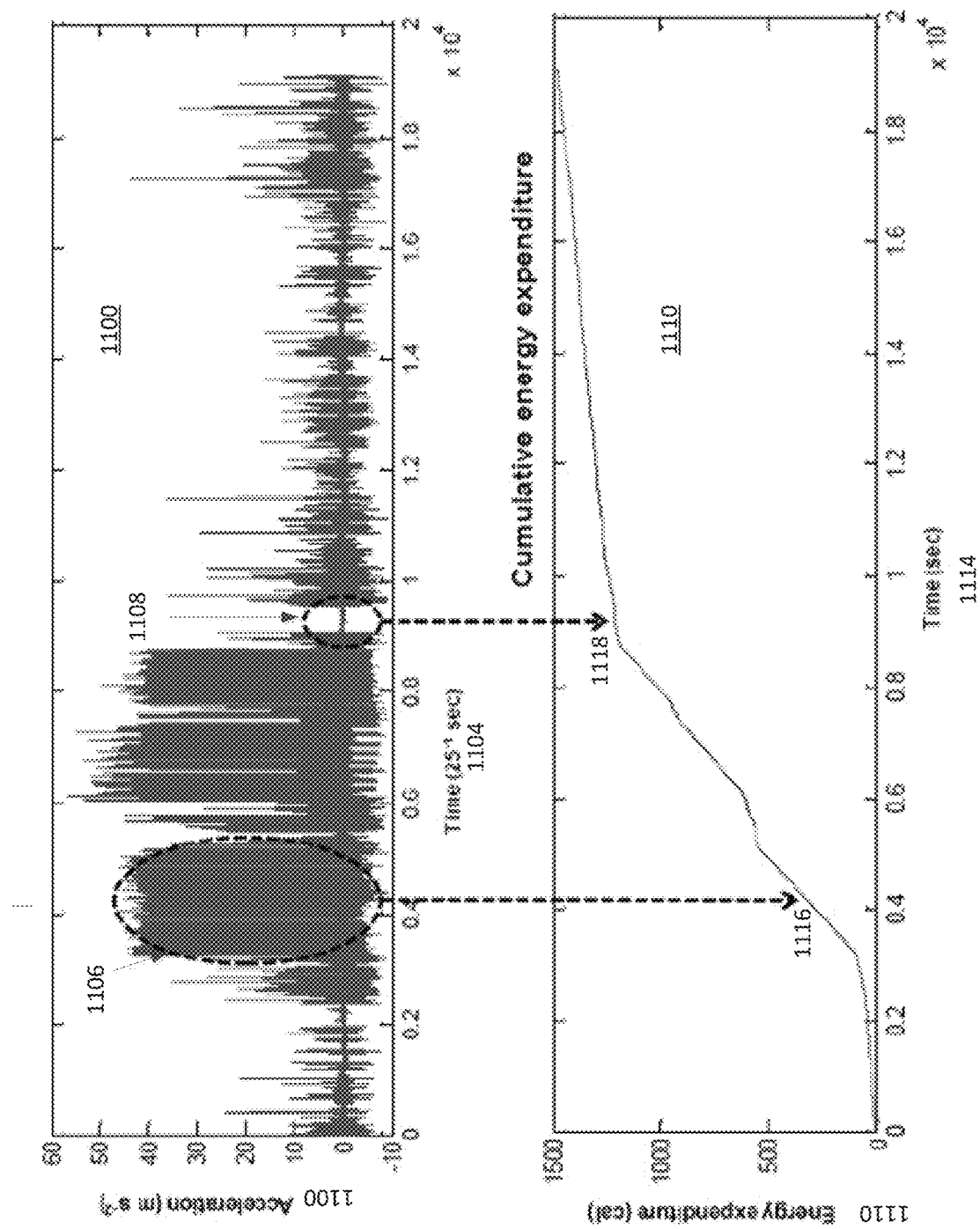
FIG. 11 graphically represents an example accumulation of energy expenditure values based on illustrative frequency data that may be implemented in some embodiments.

Further embodiments may utilize the classified activity data and/or unclassified activity data to estimate the energy expenditure of the user's detected motions as sensed by one or more of the sensors (e.g., block 308). FIG. 10 provides one example that may be implemented to determine energy expenditure. FIG. 11 graphically represents one embodiment of accumulating energy expenditure values, which may for example, be used to determine caloric burn in some embodiments.

Figure 12:
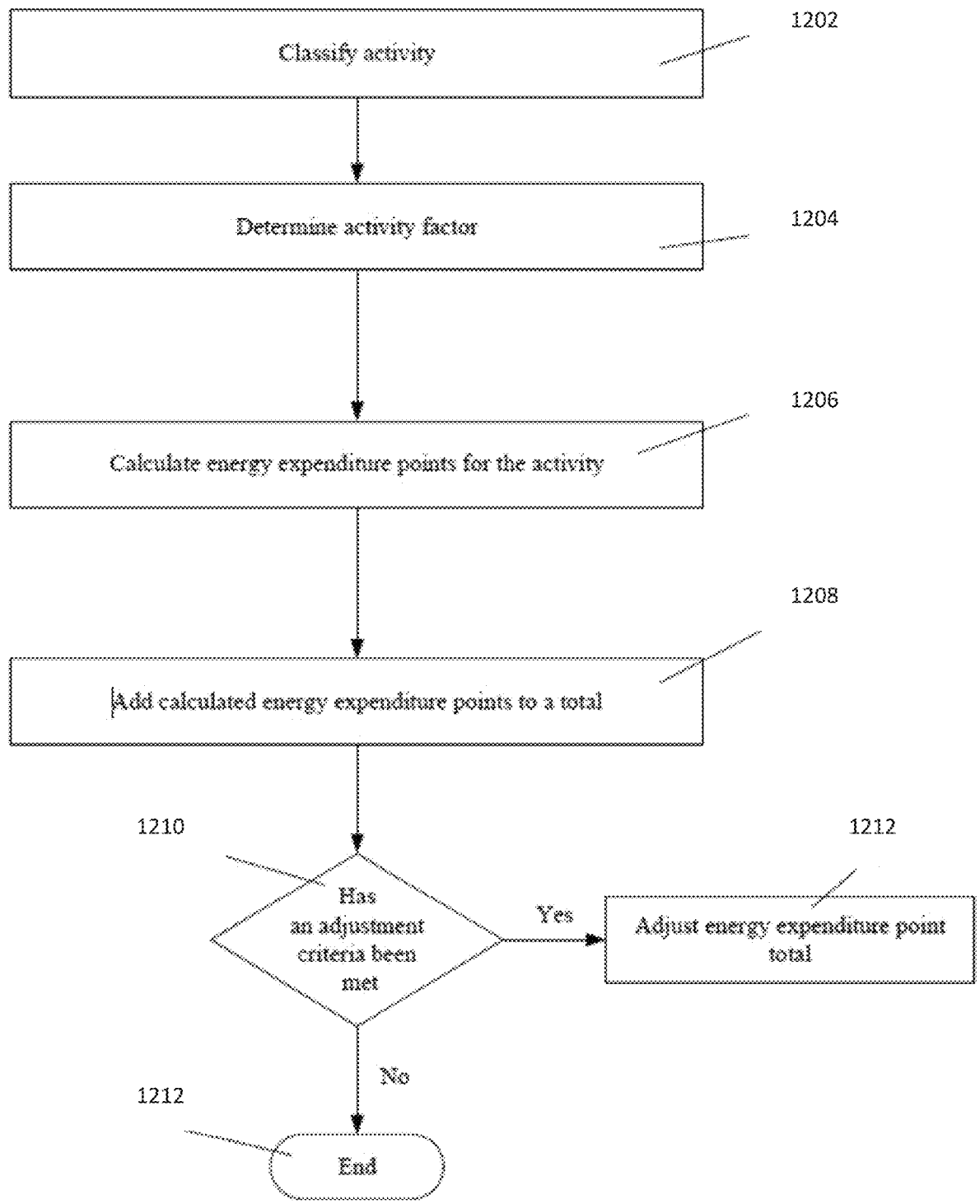
FIG. 12 shows a flowchart of an embodiment of measuring activity of a user that may be implemented in conjunction with, or independently of, other embodiments described herein.

Further embodiments relate to adjusting energy expenditure values according to at least one activity factor. In some embodiments there is not a one-to-one correlation between an activity and an activity factor. The selection of an activity factor may be based on several different variables, such as the activity identified, steps taken, heart rate, and intensity of a workout. FIG. 12 illustrates a method for calculating energy expenditure points, in accordance with an embodiment of the invention.

Aspects of various embodiments may offer one or more advantages and/or benefits over the prior-known systems and methods. In certain embodiments, false positives are reduced or eliminated for short-duration arm movements using a buffer filling strategy. Using a constrained search for analysis (e.g. FFT) may assist in selecting the correct frequency (e.g., frequencies relating a vertical bounce rather than the arm swing such that the correct walking frequency is obtained for two feet steps). In further embodiments, the overlapping of motion data windows may allow for improved detection of short bursts of activities (e.g., step activities). Finally, the frequency analysis may be performed on one combined channel of sensors so that arm rotation does not throw off detection and measurement of sensor outputs. Furthermore, by combining accelerometer channels, less analysis (e.g. Fourier transform frequency analyses) may be performed. This may improve battery life. One or more of these advantages may be realized on a portable device configured to be worn on an appendage of the user during the performance of the physical motions.

FIG. 4 shows flowchart 400 of an illustrative method that may be utilized to quantify performance of a specific activity such as steps, which may occur during walking, running, or any other physical activities of an individual. One or more processes of FIG. 4 may be implemented as part of block 304. Alternatively, one or more portions of flowchart 400 may be conducted independently of block 302 or any other process disclosed herein.

Flowchart 400 may initiate with block 402 to obtain data relating to athletic movements. The data may be calculated or otherwise obtained from the sensor data of block 302. In certain embodiments, at least a portion of any quantifications or calculations may be conducted on a portable device, including a wrist-worn device (e.g., sensor 142). Further, a single device (such as device 142/226) and/or sensor (e.g., an accelerometer) may provide data that is utilized to determine multiple different movements. Specific embodiments relate to systems and methods that may be used on a single portable device configured to be worn on an appendage (such as an arm or leg) comprise all the sensors and/or other information utilized to collect and process motion data and provide an output of the data to a user.

In one embodiment, a single multi-axis accelerometer may provide data relating to actual steps (such as detecting bounce due to stepping) and arm swing movement of a user. In one embodiment, device/sensor 226 is configured to detect bounce data from stepping of the wearer as well as collect arm swing data. In one embodiment, a single unitary device that is configured to be worn on the wrist is enabled to collect accelerometer data based upon the user's arm swings and bounce from stepping. An illustrative example of detecting arm swing and bounce data are provided below in FIG. 5.

Collecting athletic data relating to a plurality of movements, such as bounce data and arm swing data may, in certain embodiments, provide one or more benefits not obtained in prior art systems and methods, including for example: improved accuracy, and decreased latency in reporting the values. Further benefits provided by one or more embodiments not provided in the art include classification of activities that are based upon step count (or the relevant athletic movement). For example, certain individuals do not "bounce" during walking and/or running to the same extent as an "average" individual. Further, certain embodiments may result in excluding repetitive behavior from improperly being classified as a specific activity, such as for example, running and/or walking. Still yet further benefits may include improved determinations of intensity and/or speed and utilization of those determinations in activity classification, improved power consumptions, and/or a combination of these or other improvements.

Data obtained at block 402 may be obtained from one or more sensors, including either carried or worn by the user or those fixed in specific locations, such as within a wrist-worn device 226. In accordance with a first embodiment, a plurality of samples from one or more sensors may be obtained during a first time period. In one embodiment, at least one sensor comprises an accelerometer. The accelerometer may be a multi-axis accelerometer. In another embodiment, a plurality of accelerometers may be utilized. Other non-accelerometer based sensors are also within the scope of this disclosure.

Block 402 (or 302) may be obtained at a fixed sampling rate, yet in other embodiments, a variable sampling rate may be implemented for at least one of the sensors. In one embodiment, a 25 Hertz sampling rate may be utilized. In one such embodiment, utilizing a 25 Hz sampling rate to obtain accelerometer data from an appendage-worn (e.g., wrist-worn) portable device may adequately obtain data, such as for example, step counts while obtaining acceptable battery life as compared to other prior art methodologies. In yet another embodiment, a 50 Hz sampling rate may be utilized. These rates are merely illustrative and other rates are within the scope of this disclosure. In certain embodiments, the first time period may be 1 second. In one embodiment, 64 samples of data may be obtained during the first time period. Each sample of data may have multiple parameters, such as motion vectors for multiple axes, however, in other embodiments; each sample of data is a single value. Certain implementations may provide data comprising multiple values as a single value. For example, data from a 3-axis accelerometer may be provided as a single value.

The collected data may be analyzed or processed, which may occur upon collection, at predefined intervals, upon occurrence of predefined criteria, at a later time, or combinations thereof. In certain implementations, samples within the first time period may be mean centered and/or scaled.

Samples (or data relating to the received samples) from the first time period may be placed in a buffer (see, e.g., block 404). Those skilled in the art realize that one or more buffers may be part of any one or more computer-readable mediums, such as computer-readable mediums 110 and/or 112 within system memory 108. One or more systems or methods may be implemented to determine whether samples from the first time period are placed in a first buffer. One or more factors may determine whether samples from the first time period are placed within a buffer. For example, accuracy and/or reliability may be considered.

In one embodiment, about 128 samples may be placed in a first buffer. In another embodiment, the buffer duration may differ. In certain embodiments, the buffer may be about twice (e.g., 2×) the first time period. For example, if the first time period is 1 second, then the buffer duration may be 2 seconds in certain embodiments. The buffer may be a specific time duration (e.g., 2 seconds) regardless of the duration of the first time period. The buffer duration may depend on one or more factors, including for example but not limited to: battery life, desired energy consumption, sampling rate, samples obtained, a desired wait time before calculation procedures and/or combinations thereof among other considerations.

In certain implementations, the first buffer may comprise one or more sub-buffers. For example, a 128 sample buffer at a sample rate of 25 Hz may comprise two 64 sample sub-buffers. In another embodiment, a collection of data (i.e., the first buffer which may be 128 samples) may be divided equally over duration of time, such as for example, 2 seconds. For example, a first buffer may be subdivided into 4 equal sub-buffers (which may be, for example, a half second in duration). In another embodiment, each sub-buffer may correlate to about half a second of data, regardless of the size of the buffer. In accordance with one embodiment, each sub-buffer is independently analyzed from at least one other sub-buffer (and may be independently buffered from each other sub-buffer in that particular buffer).

Further aspects of this disclosure relate to optionally classifying data that may be discarded (or otherwise not used in specific analyses) before conducting further analysis (such as for example, FFT analysis). Thus, although certain process, such as block 406 may be implemented to mark, and possibly remove, extraneous data (such as data that is determined not to step or arm swing data) with one or more exclusion criterion, such data may be preserved for later analysis. As one example, peaks and/or valleys of accelerometer data may be measured to determine if they are large enough to be considered walking or running. In certain embodiments, multiple segments of a buffer may be utilized to ensure quick arm fluctuations are not misinterpreted by a device, and thus may utilize limited processing power by conducting analysis of the data, such as for example, entering a frequency analysis mode.

In this regard, certain data may not be used to determine actual steps but nonetheless may be used to determine classification of an athletic activity (e.g., walking, running, playing basketball, etc.) or calculating energy expenditure, among other determinations (see, e.g., block 407). In one embodiment, the first buffer may have data indicative of motion or other physical activity, for example, accelerometer data (alone or in combination with data from one or more other sensors) may comprise frequencies indicative of detected activity. The activity, however, may not be activity comprising steps. Example embodiments of classifying activity and calculating energy expenditure are discussed below, including data not utilized to quantify steps, may be found below in relation to discussions of at least FIGS. 9-12.

Aspects of this disclosure may utilize the sensor data to quantify activity, such as a user stepping. In yet other embodiments, steps may be detected, however, the detected steps may not signify an activity as to which the device or process is configured to detect. For example, a device (or plurality of devices) may be configured to detect walking and/or running, but not a shuffling motion commonly performed in a sporting environment, such as a basketball game. In this regard, activity within several sports may cause the user to swing their arms and/or bounce, however, are not indicative of walking or running. For example, a defensive basketball player often has to shuffle in several directions, however, is not walking or running. Aspects of this disclosure relate to increasing the accuracy of step counting, and therefore, may implement processes to remove such movements from step counting determinations. In yet other embodiments, however, such data may be used to determine that the user is performing a specific activity and implement another process based upon this finding. Further, in certain embodiments, even in certain systems and methods for quantifying step counts, activities which are considered extraneous to the intended detection, however, may be considered in further analysis, such as for a determination of activity classification.

Regardless of whether block 406 is implemented, systems and methods may be implemented to quantify steps based upon the data (or a portion thereof). In one embodiment, block 408 may be implemented to process at least a portion of the data. Analysis (and/or other statistical measures) may be performed on the entire buffer or at least one of the sub-buffers, such as for example, calculating an average (e.g., a mean value) and/or a deviation (e.g., variation or standard deviation) of data within a sub-buffer. In one implementation, one or more of the following may be performed on the sensor data: scaling, removing forces of gravity, calculating an absolute value of the data, mean centering of a value, including raw data and/or the mean-centered absolute value. Those skilled in the art with the benefit of this disclosure will readily understand that other methods may be implemented to process the data without departing from the scope of this disclosure.

In accordance with one embodiment, data (such as the data within the buffer or a sub-buffer) may be compared with a threshold as part of block 408 or another process (see, e.g., decision 410). As used herein, discussions relating to a threshold may refer to being lower and/or higher than a predetermined value or range of values. In one embodiment, vector magnitudes from the sensor data may be calculated. In further embodiments, an average value may be determined from the magnitude vectors. As one example, vector magnitude data may be calculated from an accelerometer signal, which may be utilized to determine an average value of the accelerometer signal. An average value may be calculated for every second, 5 seconds, or any duration of time. In one embodiment, the value may be compared with a first threshold for a sub-buffer which comprises data within the buffer. In one implementation, if the data within the sub-buffer does not meet a threshold, then data within an entire buffer (e.g., the first buffer) may not be utilized in further determinations of step quantification. Further logic may be utilized to determine if the sub-buffers have valid data (e.g., data that met the threshold), and if so, that data is utilized in further step count determinations. In one embodiment, contiguous segments (which may be 4 sub-buffers) must be assembled that have data (e.g., detected acceleration) above a threshold to be analyzed (such as, for example, by a frequency determination algorithm). In certain embodiments, the data of the first buffer (as opposed to the individual sub-buffers) is utilized in further determinations.

Figure 4A:
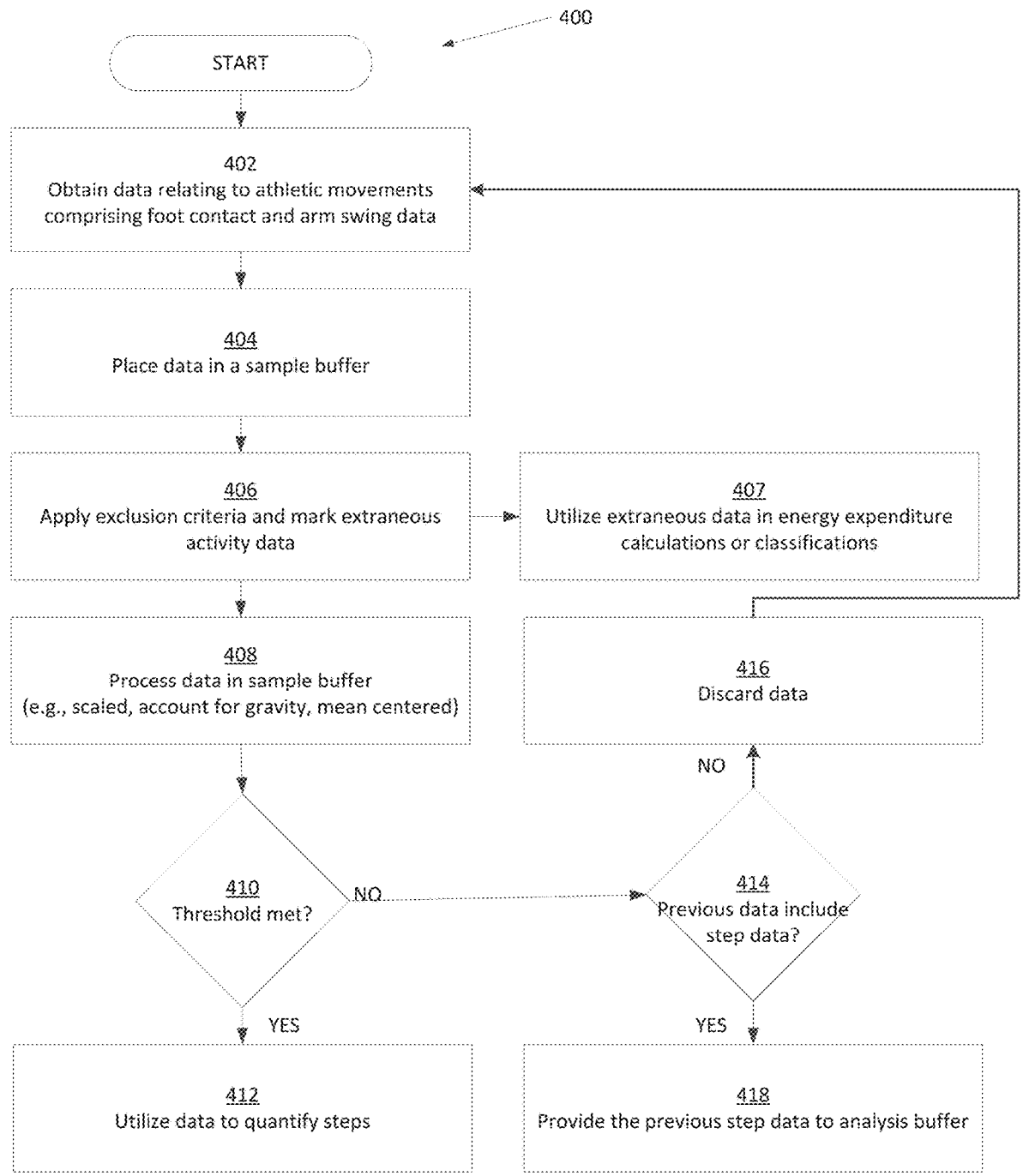
FIGS. 4A and 4B show an example flowchart that may be utilized to quantify steps in accordance with one embodiment. Specifically.
Figure 4B:
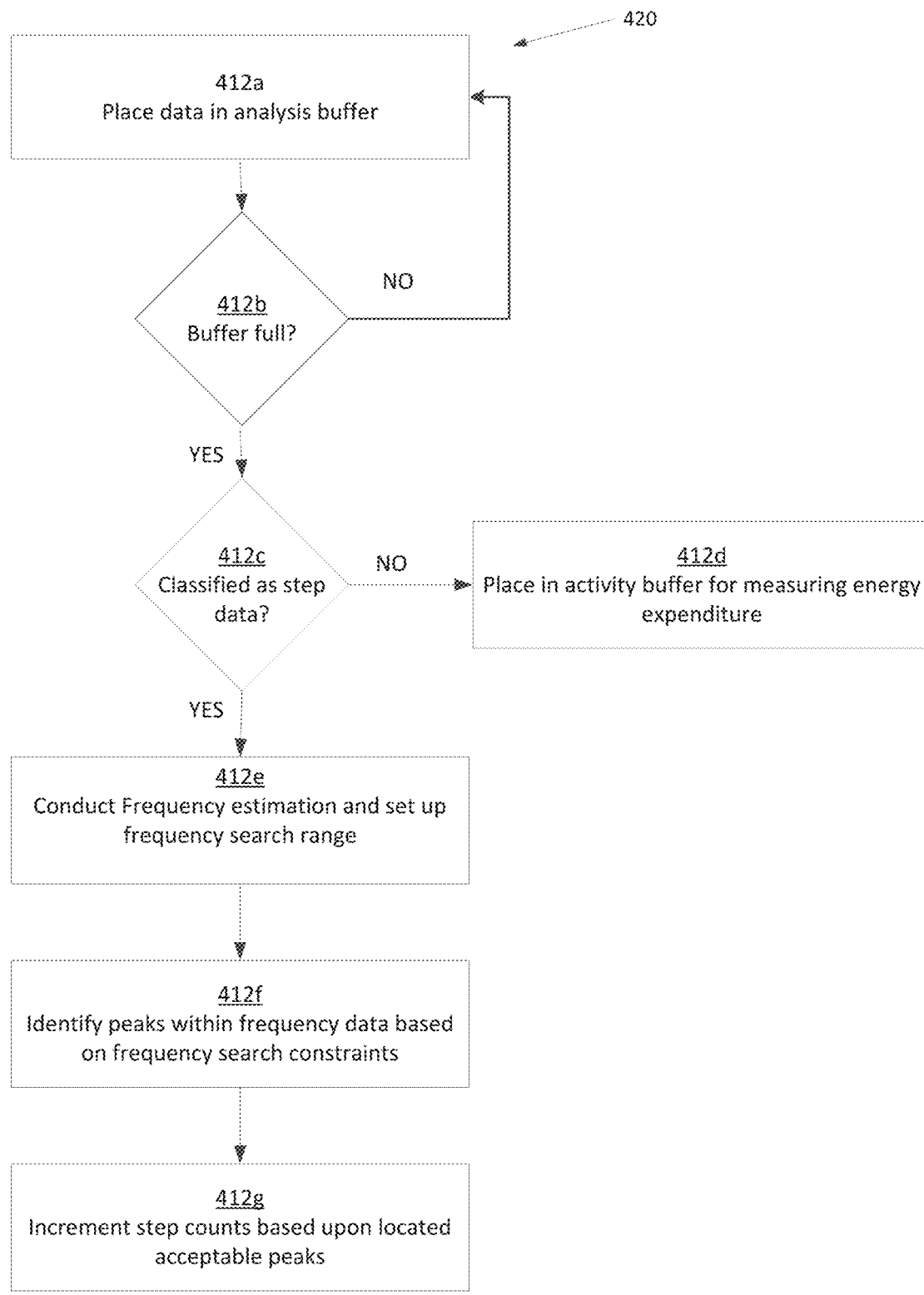

If a buffer (e.g., the first buffer or a second buffer, which may be a sub-buffer of the first buffer) meets the threshold (and/or passes other criteria, including but not limited to those described in the preceding paragraphs), that data may be utilized. For example, block 412 may be implemented to initiate utilizing the data meeting the threshold. FIG. 4B provides a flowchart 420 showing an example process for utilizing the data, which is discussed in the next paragraph. If at decision 410, it was determined that the data did not meet a threshold, decision 414 may be implemented. For example, in one embodiment, it may be determined at decision 410, that mean-centered acceleration data did not meet a threshold value, thereby indicative that there was not enough acceleration to warrant further processing such as determination of a FFT. In one embodiment, block 412 may be implemented to determine (or retrieve information regarding a determination) whether steps were detected for the previous sample buffer. If not, the data may be discarded for purposes of quantifying steps (e.g., block 416). In one embodiment, an analysis buffer comprising the data may be reset. If, however, the previous sample buffer comprised step data, block 418 may be implemented to utilize the previous step data in step quantifications processes.

Looking to FIG. 4B, flowchart 420 shows an illustrative example of one implementation of processing data that meets the threshold of decision 410. Thus, in accordance with one embodiment, flowchart 420 is an example of one implementation of block 412 and has been labeled as 412a-412f, respectively, however, those skilled in the art will appreciate that flowchart 420 may be performed, either in whole or partially, independent of block 412 and/or one or more processes of flowchart 400 of FIG. 4A. As indicated in block 412a, the data is marked or otherwise placed into an analysis buffer. In one embodiment, the data includes the average magnitude value obtained from half-second duration of activity data. In one embodiment, non-mean centered data obtained during the corresponding duration of the acceptable first buffer may be provided to the analysis buffer. Yet, in another example, derivations calculated from the data meeting the threshold of decision 410 may be placed in the analysis buffer. In one embodiment, the analysis buffer may be a first-in last-out (FILO) buffer.

Decision 412b may be implemented to determine if the analysis buffer of block 410a is full. In one embodiment, the determination may be based upon or correlated to a duration of activity data. For example, the analysis buffer may be full upon comprising 5 seconds in duration of data for one embodiment. The analysis buffer may be deemed full upon comprising a quantity of samples. In one embodiment, the analysis buffer may comprise 128 samples. In certain embodiments, the analysis buffer may be larger than the sample buffer described in relation to flowchart 400 of FIG. 4A. In one embodiment, the sample buffer may comprise 64 samples of data (which may for example correspond to 1 second duration of activity data) and the analysis buffer may comprise 256 samples of data (which may correspond to 4 seconds of activity data). The analysis buffer may comprise the same duration as the first buffer, thus may be full upon obtaining a single sample buffer. Thus, in one embodiment, an analysis buffer may consist of a single sample buffer. If the analysis buffer is deemed not full, block 412 may be conducted until the buffer is full.

Upon obtaining a full analysis buffer, decision 412c may be implemented to classify the data as step data or non-step data. In this regard, certain embodiments may utilize data within the analysis buffer for calculations of energy expenditure regardless of whether that data is considered to comprise step data or a threshold level of step data, however, still may categorize the sensed data into whether a threshold quantity of steps are detected. In one embodiment, the analysis buffer may be divided into sub-buffers. For example, a 128 sample buffer may be divided into 4 equal sub-buffers of 32 samples. In another embodiment, the respective sample buffers included as part of the analysis buffer may be utilized in any determinations. Attributes of each sub-buffer or subsection of data may be utilized. In one embodiment, variance or deviations between the data may be utilized. For example, the mean and the standard deviations of each sub-buffer or subsection may be calculated and utilized as part of decision 412c. The mean of the standard deviation may be determined in certain embodiments.

In one implementation of block 412c, activity may be deemed to comprise non-step data if any of the sub-buffers or sub-sections of data within the specific buffer comprise attributes that fail "low threshold criteria". In one embodiment, the low threshold criteria comprises a determination that a sub-buffer's attribute is less than 50% of the mean of the standard deviation of the other sub-buffers. In one embodiment, the entire analysis buffer may be deemed non-step data, yet in another embodiment, only those specific sub-buffers that fail the low threshold criteria are deemed to comprise non-step data. Further embodiments may utilize "high threshold criteria." In one embodiment, the high threshold criteria may comprise a determination whether an attribute of any of the sub-buffers are greater than 180% of the mean of the standard deviation of the other sub-buffers. Like the low threshold criteria, failing to meet the criteria may result in the entire analysis buffer being deemed non-step data, yet in another embodiments, only those specific sub-buffer that fail the high threshold criteria are deemed to comprise non-step data.

The low and high threshold criteria may be used in combination such that both must be successfully passed, yet in other embodiments, one or more criteria may be used without implementation or successful completion of the other. Failure to pass one or more criteria may result in in not conducting further step-related analysis on at least a portion of the data, however, data may be utilized for other activity-related determinations (see, e.g. block 412d). If, however, criteria are successfully met at block 412c, block 412e may be implemented to conduct frequency estimation and set up a frequency search range. In further embodiments, one or more processes described in relation of block 406 may be conducted as part of decision 412c.

Figure 5:
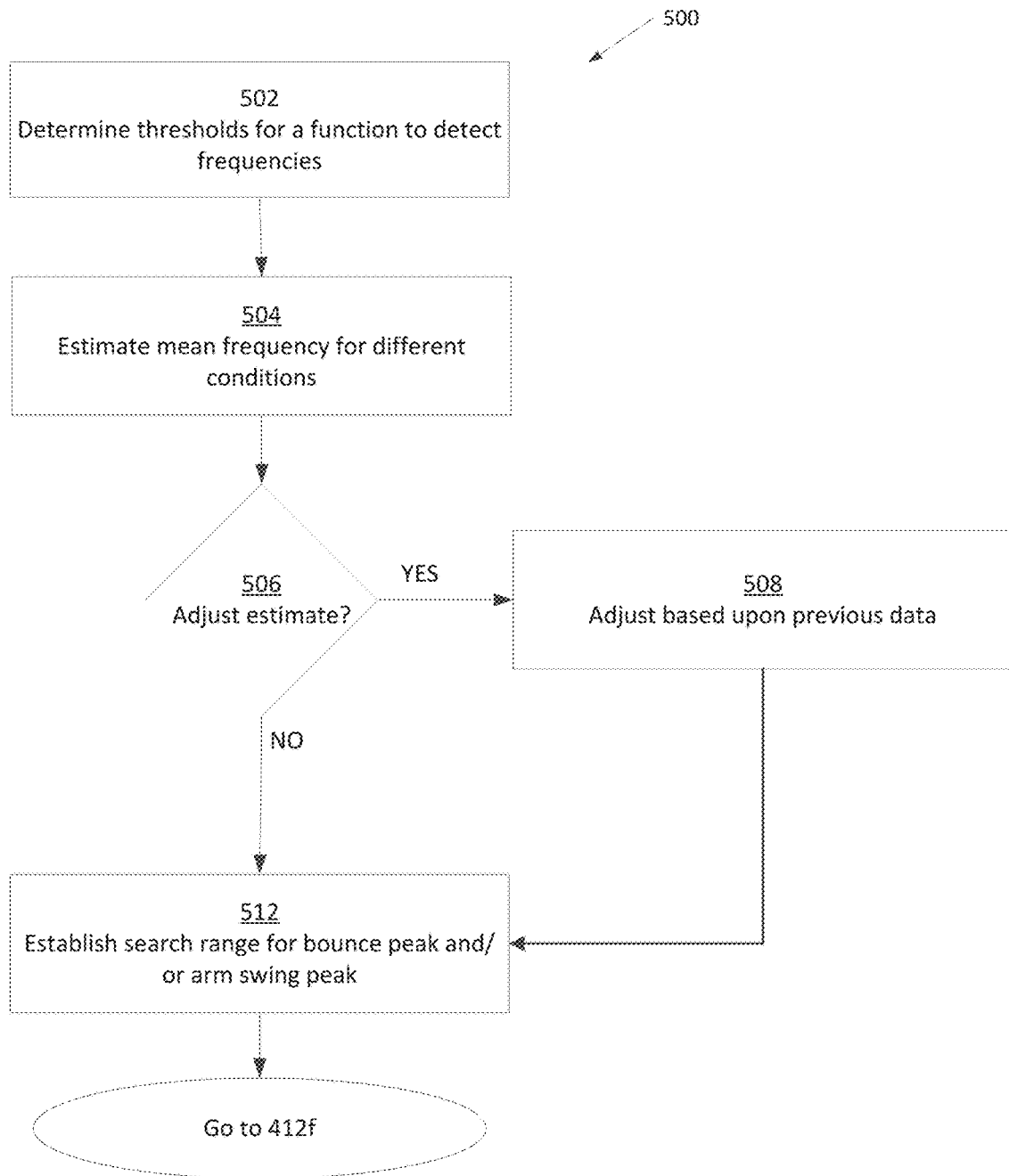
FIG. 5 shows an example flowchart that may estimate frequency and set up a frequency search range in accordance with one embodiment.

Aspects of this disclosure relate to systems and methods configured to conduct frequency estimation and setting up frequency search ranges to locate peaks. In one embodiment, peak locating systems and methods may be utilized on data within a buffer, such as the analysis buffer. Yet in other embodiments, other data may be utilized, alone or in combination with data within the analysis buffer. FIG. 5 provides a flowchart 500 showing one example process for estimating frequency. Those skilled in the art will appreciate that FIG. 5 is merely one of many embodiments that may be utilized in accordance with various implementations. Looking to flowchart 500, thresholds for a function to detect frequencies may be determined or retrieved (e.g., block 502).

One or more systems or methods for determining identification criteria for locating peaks may estimate frequency of the data points. For example, an average (such as for example, a mean value) and/or a standard deviation (or variance) may be obtained. Such data may be utilized to determine "peaks" and "valleys" (e.g., the high and low values within the data), which may be quantified. Such data may be used in determinations of dynamic thresholds and/or derivative around the peak. In one embodiment, weighted averages, such as one or two-pass weighted moving averages of data in the buffer may be utilized in any determinations. In further embodiments, raw sensor data (e.g., accelerometer signals) may also be used, either alone or in combination with other attributes, such as derivatives of the data.

In one embodiment, a 1-pass weighted moving average, a 2-pass weighted average and raw data are each used. In another embodiment, only the 2-pass weighted moving average may be used. In one embodiment, the mean and standard deviation of the derivatives are calculated and may be used as threshold levels. In one embodiment, one or more processes may be utilized to obtain thresholds. For example, a first method may be utilized to locate peaks within a fixed range. Yet in certain embodiments, a second method may be utilized to determine identification criteria for locating peaks. In certain implementations, the first, second or additional methods may be implemented based, at least in part, on battery life. For example, the second method may require additional processing power, and therefore, may not be utilized upon receiving an indication that the battery life was decreased below a set point, and/or is declining at a rate above a threshold.

Figure 6:
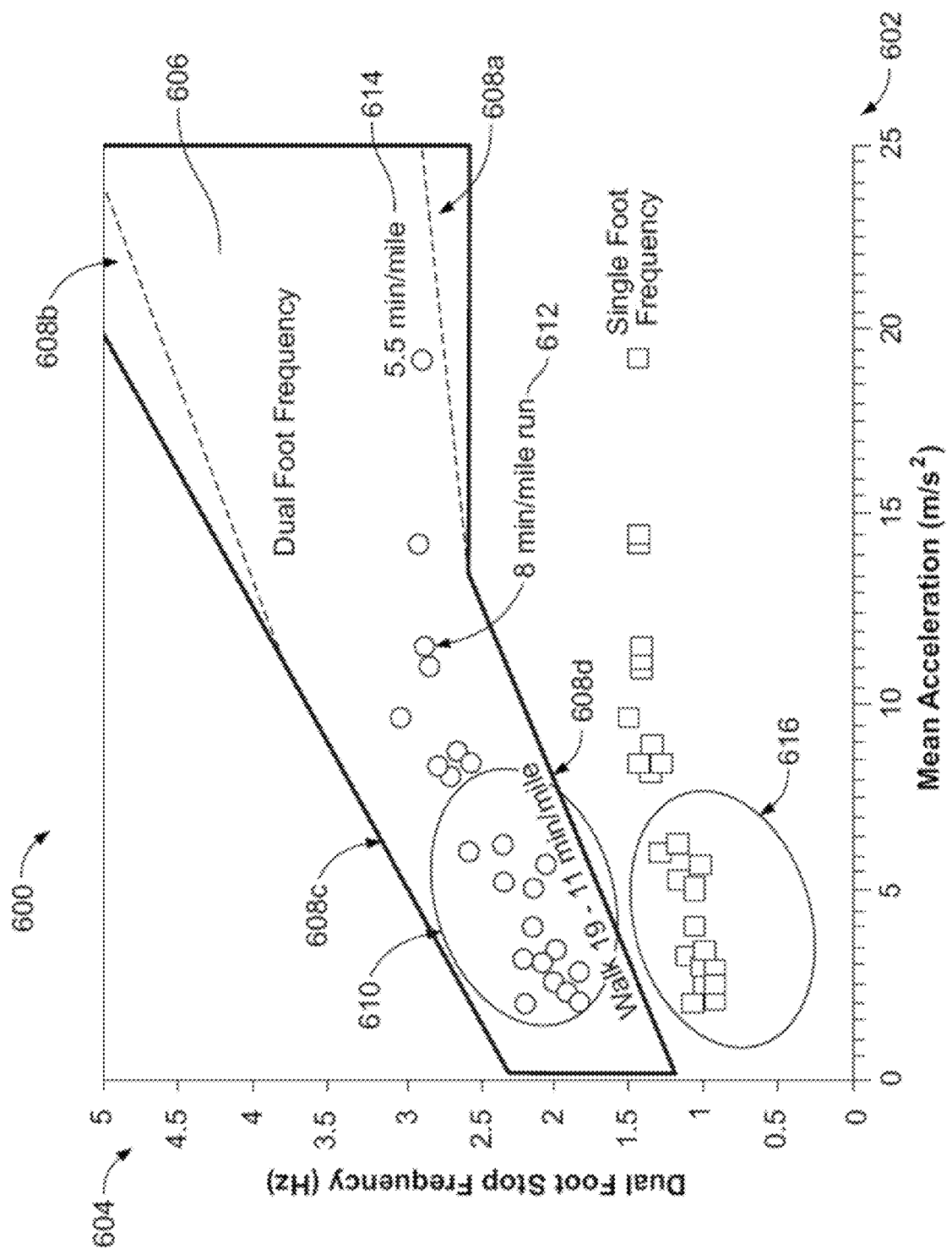
FIG. 6 shows a graph illustrating an example search range of motion data in accordance with certain embodiments.

At block 504, a step frequency may be determined for the specific buffer. In certain embodiments, a mean acceleration of the buffer may be used to create a distinct narrow search range of the data (e.g., frequencies). The search range may relate the mean acceleration to an expected walking/running (or other activity) frequency. For example, FIG. 6 shows graph 600 showing the mean acceleration (expressed in meters per second squared "m/s$^2$") along x-axis 602 and the frequency in Hertz (Hz) of the dual foot step frequency along y-axis 604. Area 606 shows the detection area, which may be constrained by boundary lines 608a-608d. One or more of boundary lines 608 may be based, at least in part, on the thresholds calculated at block 502. Thus, if accelerations generate a frequency outside the frequency range that the accelerometry predicts (e.g., outside of boundary lines 608a-608d), then certain systems and methods may not count these as steps. This may be utilized to ensure data considered to be random noise (e.g. data with different frequency content but similar acceleration magnitudes) is not counted as a specific activity (e.g. running). In one embodiment, a mean frequency may be approximated. In one embodiment, the mean frequency of sensor data measured along one or more axes may be calculated. For example, sensor data collected from one or more accelerometers may be used to determine the mean frequency along one or more of the x, y and z axes. For example, arm swing data may comprise components along each of the three axes, and thus measured. In one embodiment, the mean frequency for multiple axes may be approximated by examining the number of peaks and/or valleys in the data.

As shown in FIG. 6, the utilization of boundaries, such as boundaries, 608a-608d will remove consideration of at least a portion of signals that are not likely to be walking and/or running (or another activity being selected for). For example, as explained below in relation to FIG. 9, signals within the range of 0.5-2.4 Hz (located along y-axis 604) may be considered as indicative of walking (see, e.g., samples designated by 610). In another embodiment, signals within the range of 2.4 to 5 Hz may be considered as indicative of running. For example, data points 612 may indicate the athlete is running an 8-minute mile and data point 614 may indicate that the athlete is running a 5.5 minute mile. Further potential uses for this data as classification of the data as comprising "walking", "running" or other activity data is discussed below in relation to FIG. 9; for example, changing activity classification may be determined based upon the frequency and the sum of the standard deviation for 2 portions of data.

In one embodiment, this (and/or other data) may be examined to determine whether a plurality of consecutive values are within a standard deviation of the mean. In one embodiment, this analysis may be conducted over a plurality of samples. Further, in certain embodiments, arm swing data may be utilized to determine the dual foot step frequency (see axis 604). For example, if a wrist-worn device is configured to measure arm swings, such data may be interpreted as the single foot frequency. In this regard, single foot frequency data points designated by element 616 may correspond to half the value (with respect to the y-axis 604) to data points 610. In one embodiment, therefore, the value of the single foot frequency may be doubled to arrive at the dual foot step frequency value. Those skilled in the art will appreciate that graph 600 is no required to be generated or displayed, but rather is illustrated herein to demonstrate aspects of this disclosure.

Decision 506 may be implemented to determine whether to adjust the estimated step frequency. In one embodiment, decision 506 may consider whether steps were counted (or the frequency of steps) in the previous buffer. For example, decision 506 may determine whether a successful FFT located steps in the previous buffer. As would be appreciated in the art there may be situations in which the data (e.g., frequencies) change, however, the user may still be conducting the same activity, albeit at a different rate or pace. For example, if a user is running at 10 mph and slows to 5 mph, he/she may still running, although at a slower pace. In this situation, however, the frequency detected will be altered. Certain embodiments may utilize linear combinations to quantify steps. For example, if at block 506, it is determined that previous data indicated that the user was walking or running, then in accordance with one embodiment, the next set of data may utilize this previous data in any determinations, such as in a linear combination, such as via block 508. In one embodiment, if there are a first quantity of sections of the buffer duration that are classified as "running" and a second quantity of section classified as "walking", systems and methods may be utilized to determine whether the user has merely adjusted their stride or otherwise changed their speed. In one embodiment, at least a portion of the samples within the buffer may be deemed to be within a specific category regardless of the data for that portion. For example, if samples were collected for 10 intervals and 9 of them were classified as running and only a single one was classified as walking, then the entire duration may be deemed running at block 508. In one embodiment, an interval may only be deemed a different category if it is immediately preceded and/or proceeded by data indicative of a consistently different category.

In certain embodiments, an indication that the user is not walking, running or performing another predetermined activity, would prevent or cease utilizing linear combinations of data in step counting determinations. For example, this may occur when a user has ceased stepping (e.g., no longer walking or running). Thus, systems and methods may prevent or cease any linear combination processes. In one embodiment, step quantification may be determined absent linear combinations, such as for example, by identifying peaks as discussed above. The estimate (which may have been adjusted via block 508) may be used to establish a search range for bounce peak and/or arm swing peak within the data (See, e.g., block 512).

Block 412f may be implemented to identify a sub-group (or sub-groups) of peaks within the frequency data to utilize in the determinations of step quantification. In one embodiment, a FFT is performed and peaks in the FFT spectrum may be identified, such as with the thresholds and/or derivative around the peak. The performance of the FFT may occur before, during, or after initiating frequency estimation processes, such as one or more processes described in relation to FIG. 5. In further embodiments, the FFT may utilize one or more threshold and derivatives derived from one or more process of flowchart 500. In on embodiment, a specific peak (or peaks) within the data (such as for example, data obtained within the first buffer and/or data obtained during first time frame) may be utilized. This may be conducted based upon determining that linear combination cannot be used. In one embodiment, "bounce peaks," "arm swing peaks," and/or other peaks may be identified. For example, many users "bounce" upon landing their feet when running. This bounce may provide frequency peaks within the data. Other peaks (and/or valleys) may be present within the sensor data. For example, many users often swing their arms in a predictable manner during running and/or walking to provide "arm swing peaks". For example, arms usually swing along an anterior/posterior axis (e.g., front to back). This frequency may be about half the frequency of the "bounce peaks". These peaks, however, may each vary independently, based upon, for example, the individual, the type of motion, the terrain, and/or a combination thereof.

Figure 7A:
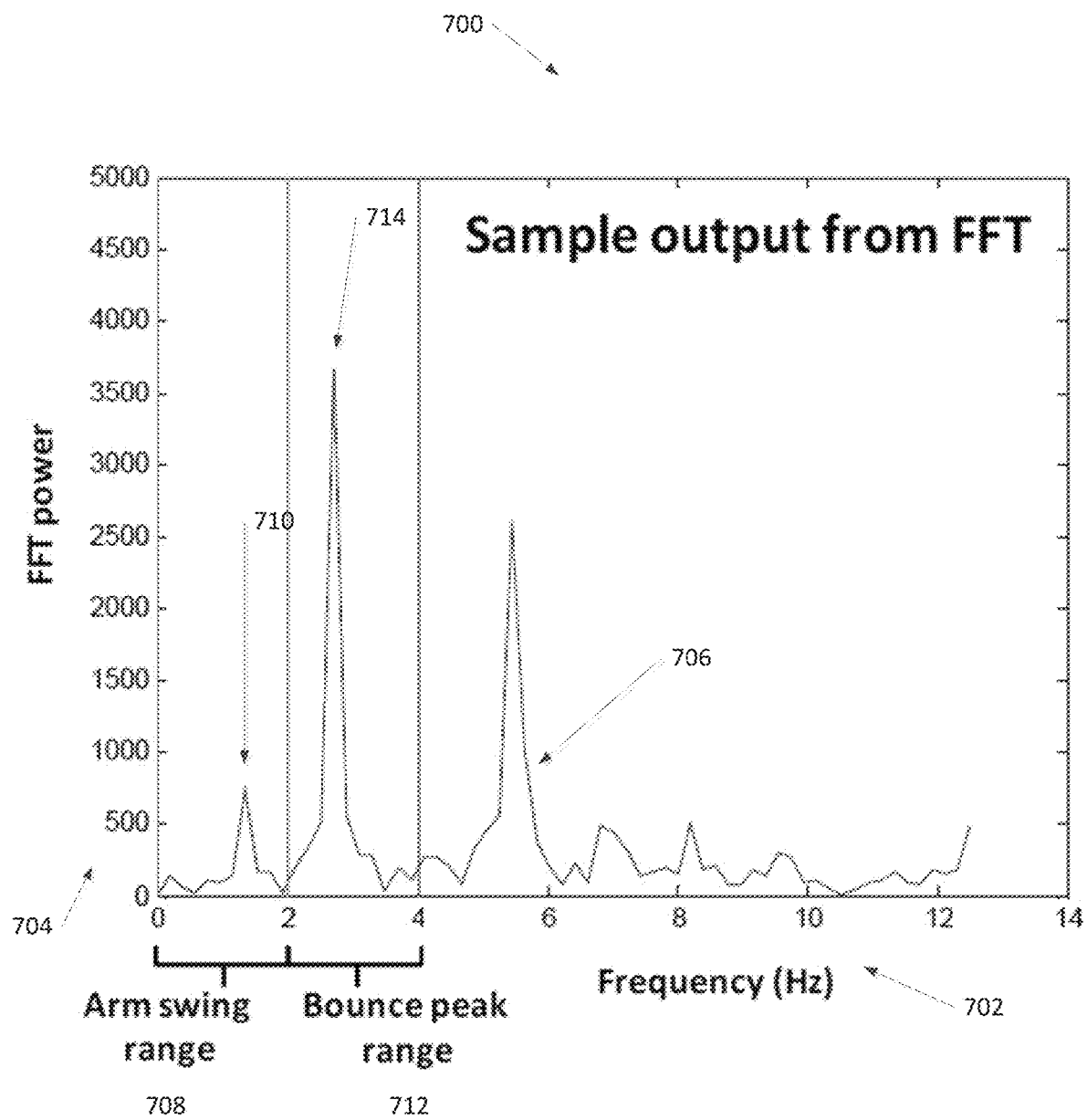
FIGS. 7A and 7B show a graph illustrating a sample FFT output. Specifically.

FIG. 7A shows graph 700 of an example FFT output of sensor data, such as multi-axis accelerometer data. Graph 700 shows the frequency in Hertz (Hz) along x-axis 702 and FFT power along y-axis 704. Line 706 plots the frequency (along x-axis 702) against the power (along y-axis 708), wherein the magnitude or maximum height along the y-axis 704 provides the maximum FFT power for a peak. The peak magnitude indicates the relative strength of the frequency, and may be used as an indicator whether a person is stepping. Those skilled in the art will appreciate that graph 700 is not required to be generated or displayed, but rather is illustrated herein to demonstrate aspects of this disclosure.

As further seen in FIG. 7A, arm swing range 708 is shown between about 0 and 2 Hz along x-axis 702 and comprises arm swing peak 710. Bounce peak range is shown at about 2-4 Hz along the x-axis 702 and comprises bounce peak 714. Thus, in the illustrated example, the frequency of the bounce peak 708 within bounce peak range is generally twice the frequency of the arm swing peak. Thus, systems and methods may identify peaks (and/or valleys) based upon the established thresholds. In this regard, computer-executable instructions of one or more non-transitory computer-readable mediums may be executed to determine if a threshold quantity of peaks are located within the range (either fixed or dynamically determined). If no peaks within the range are located, that buffer may be emptied (or otherwise not utilize that data in step counting determinations). In this regard, the peaks may refer to the frequencies may be measured by those with the highest quantity of occurrences and/or highest absolute value.

Figure 7B:
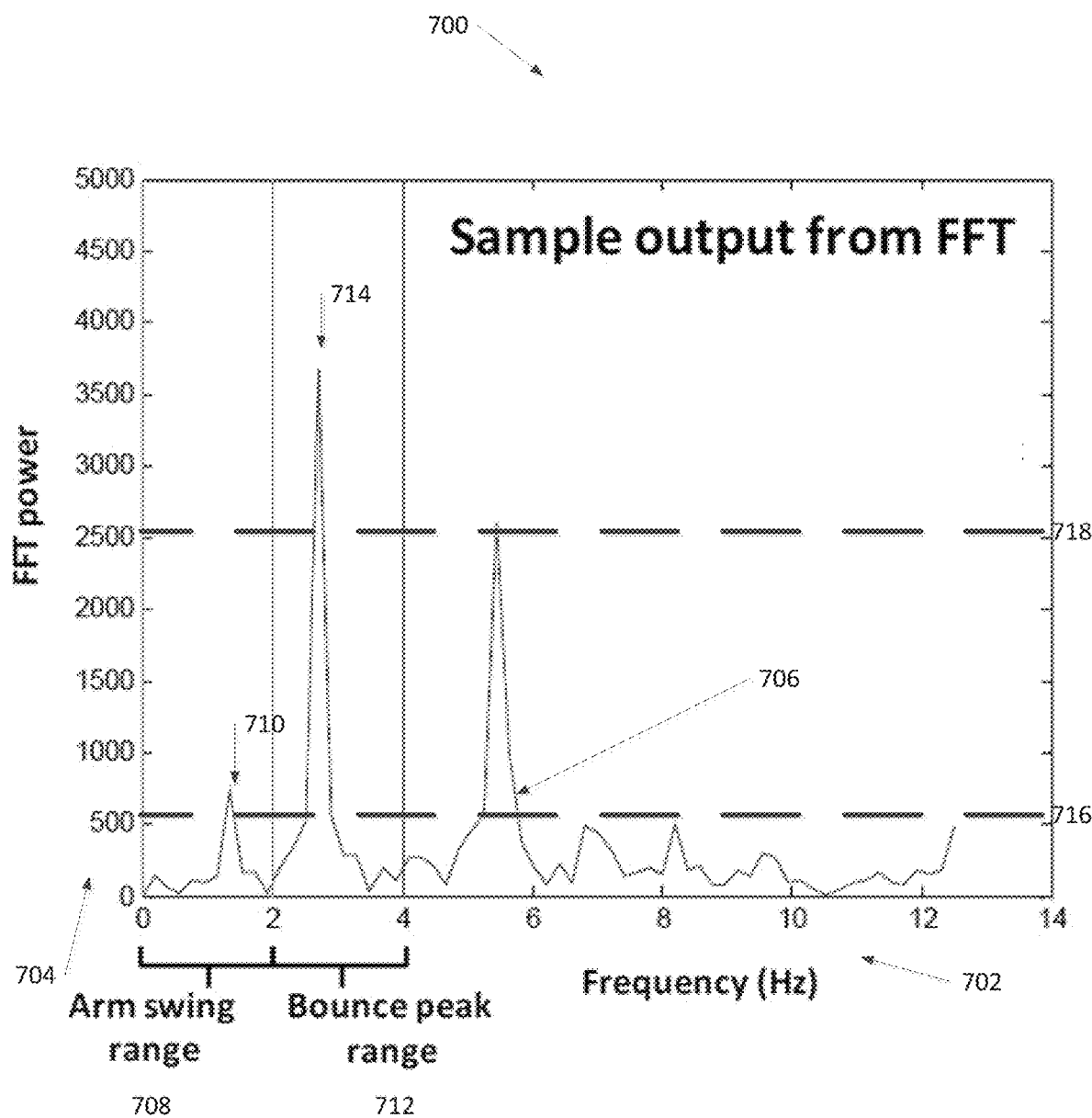

Certain embodiments may determine whether peaks (e.g., arm swing peak, bounce peak, and/or any other peak) meet a threshold. In one embodiment, a threshold of the frequency power within the constrained search range may ensure that the frequency is not simply noise and that it is large enough to be considered an activity (such as, for example, walking or running). In yet another embodiment, an overlapping window strategy may be utilized. For example, FFT windows may be analyzed in an overlapping fashion to make sure short term duration steps are counted. FIG. 7B shows graph 700 as substantially shown in FIG. 7A, however, further includes arm swing threshold 716 and bounce threshold 718. As shown, peaks within arm swing range 708 (between 0-2 Hz) may only be counted if their magnitude meets a threshold of FFT power (e.g., threshold 716 is at about 500 as shown on the y-axis 704).

Likewise, in certain embodiments, peaks within bounce peak range (2-4 Hz) may only be counted if their magnitude meets a threshold (such bounce threshold 718, which is at about 2500 as shown on the on the y-axis 704). In certain embodiments, peaks that meet or exceed a threshold may be counted as steps (see, block 412g). The steps may be incremented for a set time, such as the duration of the FFT analysis window. Certain embodiments may continue incrementing with overlapping windows. In one embodiment, steps may be quantified for each sample buffer or a certain portion (e.g., 25%) of the analysis buffer and if the threshold is met, then steps may be counted for the specific sample buffer or portion of activity buffer. If, however, the threshold for that sample buffer or portion is not met, then steps for the remaining portion of the activity buffer (or specific surrounding samples) is determined based upon the step frequency. For example, if analysis buffer comprises 4 sample buffers and only the first 3 have steps, then the step count for ¾ of that analysis buffer may be based upon the previously selected step frequency.

Further aspects relate to selecting which peaks, if any, are utilized. In accordance with one embodiment, systems and methods may select which peaks are to be utilized in quantifying steps despite the fact that the located peaks are deemed valid or meet a threshold. As discussed above, bounce data from foot contact may be more reliable arm swing data in some circumstances. Equally, arm swing data may provide more accurate results in other embodiments. In still further instances, using both peaks (and/or others) together to derive a range of data may provide the best results. Embodiments disclosed herein relate to systems and methods that may be used on a portable device configured to be worn on an appendage (such as an arm or leg) to collect activity data and determine which peaks to utilize in quantifying steps (and possibly in further embodiments, activity type and/or energy expenditure). In this regard, combinations of various peaks may be used to determine specific activities of the athlete. In certain embodiments, systems and methods may be configured to dynamically determine whether to use bounce peaks, such as for example peak 714 or arm swing peaks, such as peak 710. The determination may be updated in substantially real-time (such as every 0.5 seconds, 1 second, 2 seconds, 4 seconds, etc.) and based upon the activity data.

FIG. 8 shows example flowcharts that may be implemented to determine whether to utilize arm swing frequency or bounce frequency in accordance with one embodiment. As shown in FIG. 8, the systems and methods may be implemented to select relevant frequency peaks out of the illustrative FFT output to determine which data provides the most accurate results (e.g., a which frequency from an FFT analysis of accelerometer data should be utilized). In certain embodiments, step frequency may be used in the generation of a step count for the period of time represented by the FFT spectrum.

In one embodiment, the "relevant" peaks may include arm swing peaks and bounce peaks. Block 801 may be implemented to quantify the number of identified peaks within the corresponding search range. Thus, the bounce peaks located in the frequency estimation for the bounce range ("BR") (see, e.g., range 708 comprising frequencies between 0-2 Hz of FIG. 7A) may be quantified and the arm swing peaks located in the frequency estimation for arm swing range ("ASR") (e.g., range 712 comprising frequencies between 2-4 Hz of FIG. 7A) may also be quantified. In certain embodiments, the quantity of identified peaks (and/or quantity of specific peaks identified) may be utilized to determine which of the estimated step frequencies (e.g., determined by the ASR, BR or peaks in other ranges) may utilized. For example, decision 802 may determine whether there is at least 1 peak in the BR or at least 1 peak in the ASR. If not, block 804 may be implemented to register that no steps were performed in the specified range. If, however, there is at least 1 BR or at least 1 ASR peak at decision 802, decision 806 may be implemented to determine if there is only 1 BR peak (and zero ASR peaks) or alternatively, if there is 1 ASR peak (and zero BR peaks). If it is determined that there is only the 1 ASR peak, then block 808 may be implemented to mark the step frequency at 2*ASR frequency. Alternatively, if it is determined that there is the one BR peak, then block 810 may be implemented to mark the step frequency as corresponding to the BR frequency. As a third alternative, if there are more than only 1 ASR or only 1 BR in absence of each other, then decision 812 may be implemented. Before discussing decision 812, it is worth noting to the reader that FIG. 8 (and other flowcharts provided herein) include several decisions, such as for example, decisions 802, 806, 812 and 814. Those skilled in the art with the benefit of this disclosure will readily appreciate that one or more decisions may be grouped into a single decision and/or placed in different order, such as incorporating decision 804 within decision 802. Thus, the use of a plurality of decisions in the current order is merely for illustrative purposes.

One or more processes may determine whether there are exactly 1 BR peak and 1 ASR peak (see, e.g., decision 812). If not, block 824 (which is discussed below) may be implemented. If so, however, decision 814 may be implemented to determine whether the ASR peak is within a set range of the BR peak. In one embodiment, decision 814 may determine whether the ASR peak is within +/−15% of the ½*BR peak. If so, block 816 may be implemented to determine that the step frequency is the mean of the BR peak and 2× the ASR frequency.

If, however, the ASR peak and the BR peak are not within the identified range threshold, then block 818 may be implemented to calculate the distance from the estimated frequency for each peak. One or more processes may then determine whether the magnitude of at least one of the peaks is greater than a threshold. For example, decision 820 may be implemented to determine if the magnitude of both peaks are greater than a threshold. If the threshold(s) of decision 820 are not satisfied, block 821 may be implemented to select the frequency and magnitude of the larger of the two peaks. If the magnitude of the peaks, however, are greater than a threshold, then step frequency and peak magnitude may be chosen from the peak closer to the estimated step frequency (e.g., block 822).

Figure 8A:
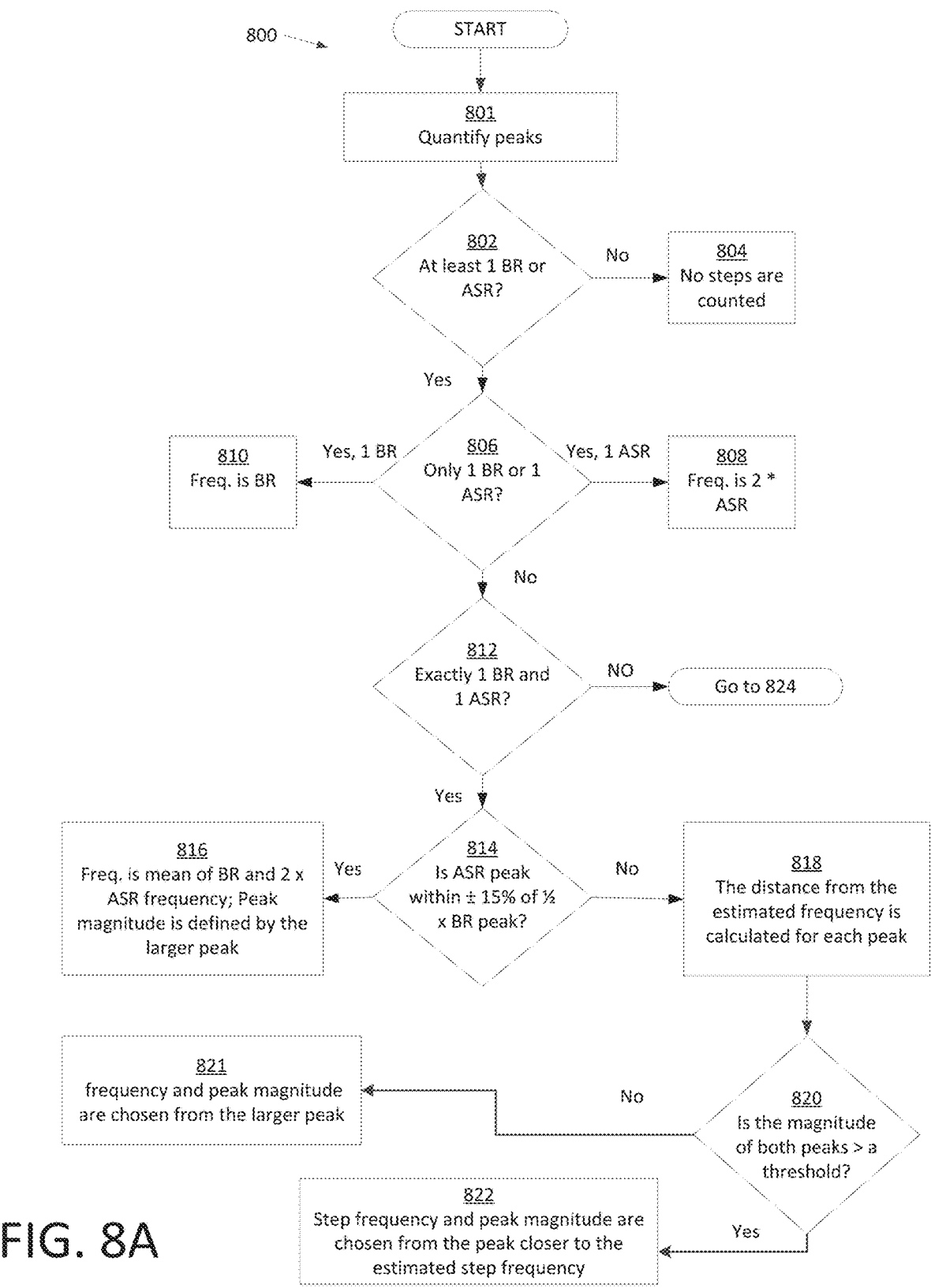
FIGS. 8A and 8B show example flowcharts that may be implemented in determinations of whether to utilize arm swing frequency, bounce frequency and/or other frequencies in accordance with one embodiment.
Figure 8B:
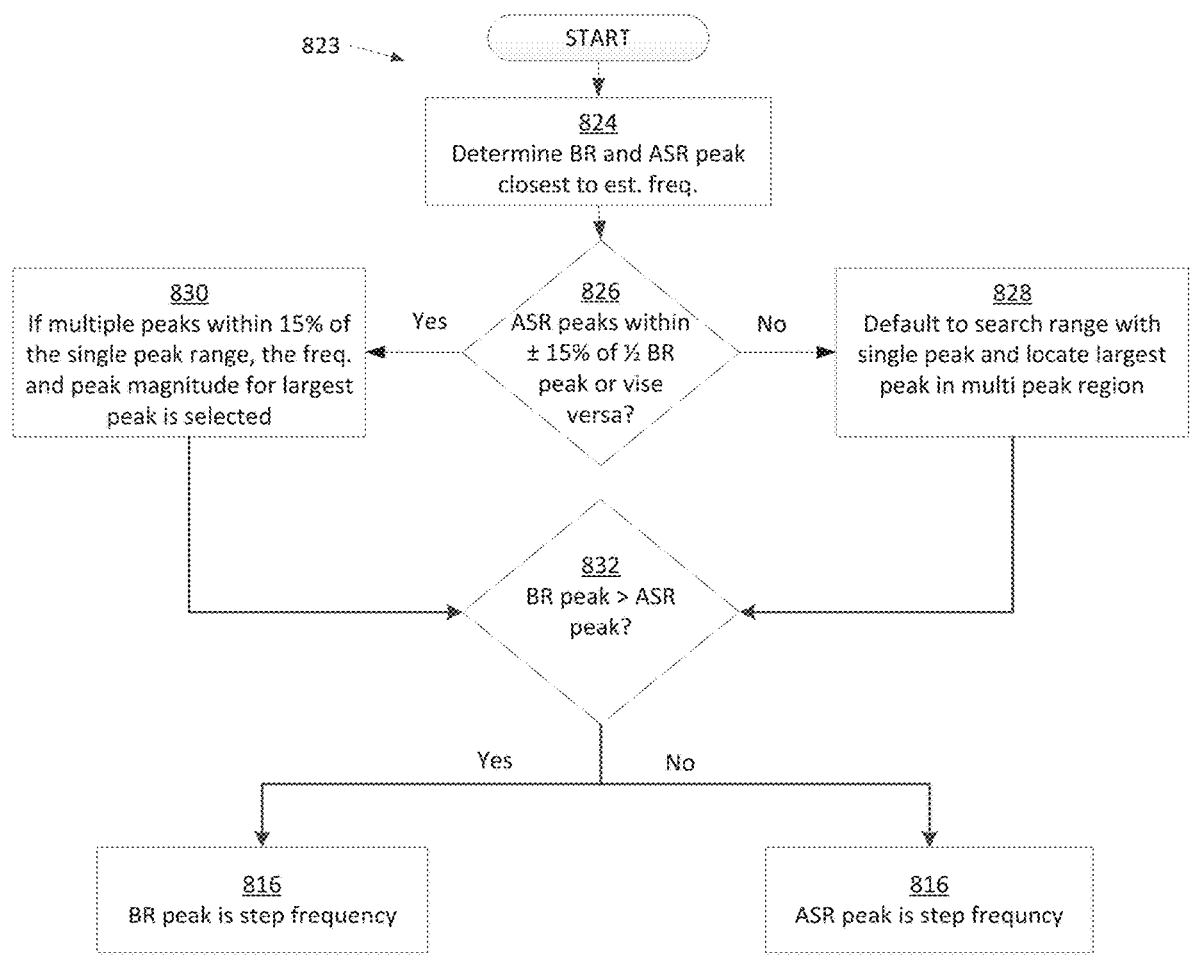

Looking to FIG. 8B showing flowchart 823, systems and methods may be configured to determine the step frequency when there are more than 1 BR peak and more than 1 ASR peak in the search range. In one embodiment, block 824 may be utilized determine the step frequency when there are more than 1 BR peak and 1 ASR peak in the data. Block 824 may be implemented upon determining that there is not exactly 1 BR peak and 1 ASR peak at decision 812 of FIG. 8A, yet in other embodiments, block 824 is independent of decision 812 and/or FIG. 8A. Block 824 may determine peak proximity to an estimated frequency, such as the frequency estimated by a frequency estimator (see, e.g., block 412e and flowchart 500). In one embodiment, the BR peak and ASR peak closest the estimated frequency are determined. Decision 826 may be implemented to determine whether at least one identified ASR peak is within a set range of the BR peak and/or whether at least one identified BR peak within a set range of the ASR peak. In one embodiment, decision 826 may determine whether the ASR peak is within +/−15% of the ½*BR peak or whether the BR peaks are within +/−15% of ½*ASR peak.

If it's determined at decision 826 that the threshold range set is not met, then block 828 may be initiated to default to a search range with a single peak and locate the largest peak in the multi-peak region. Alternatively, block 830 may be implemented if a criterion set forth in decision 826 is satisfied. In one embodiment, if there are multiple peaks within the set range set forth in decision 826 (e.g., 15%) of the single peak range, block 830 may be implemented to select the frequency and peak magnitude for the biggest peak. Decision 832 may be implemented to determine which of the identified peaks are larger. For example, decision 832 may determine whether the BR peak is larger than the ASR peak (or vice versa). Decision 832 may merely determine which of the BR peak and the ASR peak is larger. In one embodiment, the larger of the two peaks may be selected as the step frequency (see, e.g., blocks 834 and 836).

Figure 9:
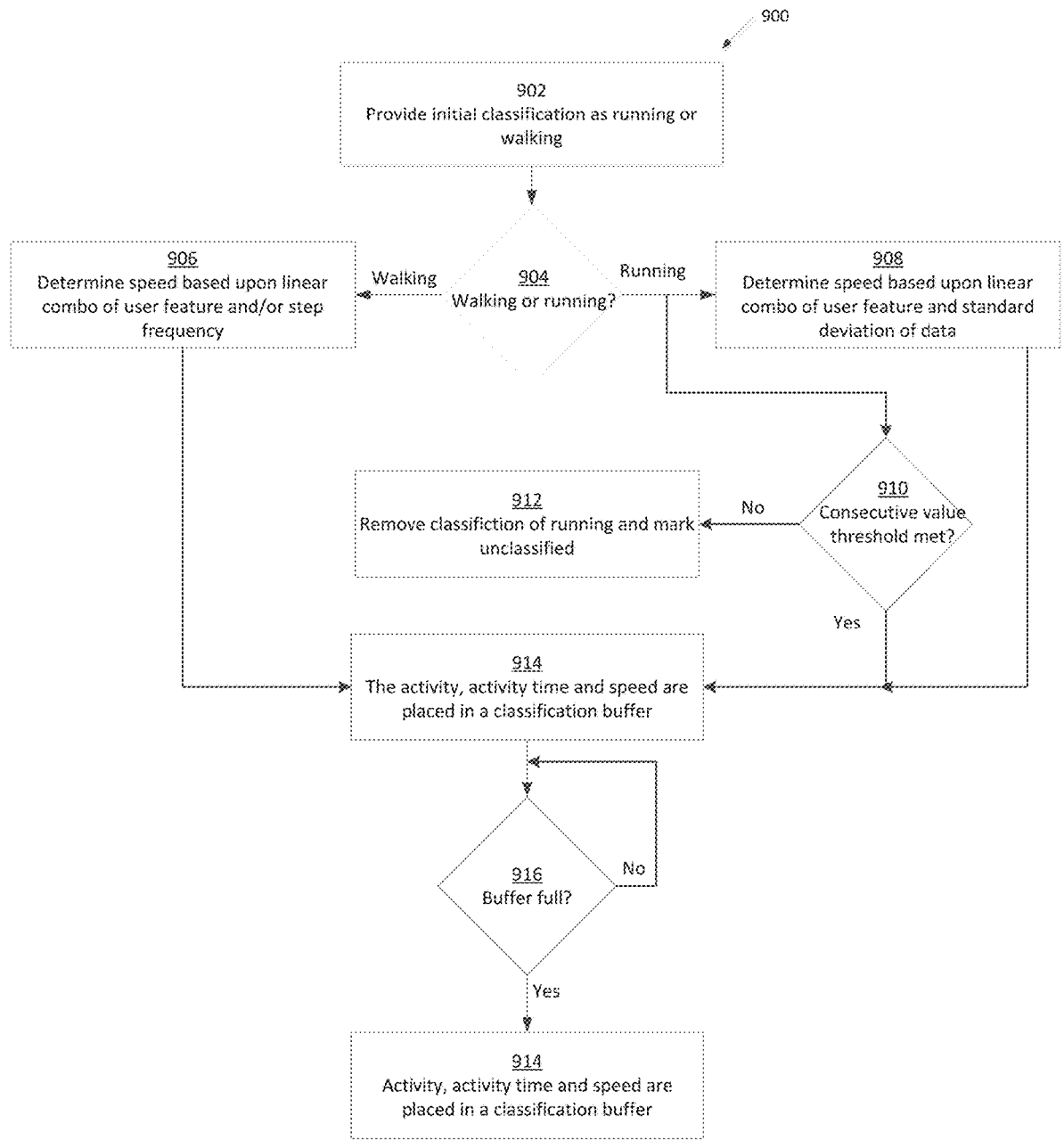
FIG. 9 shows an example flowchart that may be implemented to classify activity and determine speed in accordance with one embodiment.

Further aspects of this disclosure relate to classifying the user's athletic or physical movements based upon the sensor data. Embodiments disclosed herein relate to systems and methods that may be used on a portable device configured to be worn on an appendage (such as an arm or leg) to collect activity data and use the collected activity data to determine what activity the user is engaging in. FIG. 9 is flowchart 900 showing an illustrative example of classifying activity and optionally determining speed in accordance with one embodiment. For simplicity, the activity classifications provided in flowchart 900 are "running", "walking, and "other," however, those skilled in the art will appreciate that other classifications may be implemented in view of this disclosure.

Looking to flowchart 900, the activity may be initially classified as walking or running based upon prior analysis of the sensor data (see, e.g., block 902). This may occur in the same device that collected the sensor data and/or conducted the FFT analysis. In one embodiment, the device is configured to be worn on an appendage, such as the user's wrist. In one embodiment, the classification (e.g., as either running or walking) may be based upon the frequency content of the data. For example, the FFT-selected step frequency and time period information may be utilized to initially classify the activity. The activity classification determination may be updated in substantially real-time, such as immediately upon completion of the step quantification.

As discussed in relation to FIGS. 6 and 7, data meeting a threshold may be utilized to determine if the quantified steps are running or walking (or other activities). In certain embodiments, the "signature" of the signals may be utilized in determining whether the user was walking or running (or perhaps, conducting another activity). Signals having a certain range of step frequencies may be indicative of walking, while others may be indicative of running. Magnitude data may also be used to determine activity classifications in certain embodiments. Changing categories for adjacent data may be based upon the changing "signatures."

In one embodiment, the analysis buffer may be initially classified as a specific activity at block 902. Yet, in other embodiments; a separate buffer may be utilized that has a different duration than the sample and/or analysis buffer. Although, a classification buffer may have a different duration than a first buffer, there is no requirement that these (or other) buffers are distinct buffers; rather the second buffer may be a collection of several first buffers and or a logical extension of other buffers. In this regard, collected data may be stored in a single location but utilized (even simultaneously for two different buffers, processes, and/or analyses).

Further, surrounding data may be used to classify specific sections of data. For example, if a previous section data (e.g., at least two data values) indicated that the user was walking or running the next set of data may utilize the prior data in any determinations, such as in a linear combination. In one embodiment, if there are a first quantity of sections of the buffer duration that are classified as "running" and a second quantity of section classified as "walking", systems and methods may be utilized to determine whether the user has merely adjusted their stride or otherwise changed their speed. In one embodiment, at least a portion of the samples within the buffer may be deemed to be within a specific category regardless of the data for that portion. For example, if samples were collected for 10 intervals and 9 of them were classified as running and only a single one was classified as walking, then the entire duration may be deemed running. In one embodiment, an interval may only be deemed a different category if it is immediately preceded and/or proceeded by data indicative of a consistently different category.

According to one embodiment, if the activity is initially classified as walking (e.g., at decision 904), the speed of the walking activity may be calculated (see, e.g., block 906). Speed may be calculated based upon the step frequency and/or a feature of the user. For example, in one embodiment, the speed may be calculated based on the linear combination of the user's height and the step frequency. Those skilled in the art will appreciate that other features, including but not limited to, sex, weight, and/or other features may be utilized.

If the initial classification is running, then in one embodiment, final determination of the activity classification (and optionally speed) may be calculated using the standard deviation (or variance) of each data chunk in the analysis buffer. In one embodiment, speed may be determined based upon based upon the step frequency, standard deviation and/or a feature of the user. In one embodiment, the speed may be calculated based on the linear combination of the user's height and the standard deviation of the data chunks in the specified buffer (e.g., the analysis buffer). Final determinations of the activity classifications may be performed. In one embodiment, the standard deviation (or variance) for values or groups of values in the analysis buffer may be utilized. For example, in one embodiment, a plurality of consecutive values (or groups of values) may be examined to determine whether a threshold level of consecutive values is met (See, e.g., decision 910). In one implementation, the values may be used to confirm whether there are a number, such as 3, of consecutive values within one standard deviation of the mean is met for 4 consecutive total values.

Decision 910 may be conducted independently of the result of determining speed in block 908. In one embodiment, decision 910 may be conducted during at least part of the performance of block 908, yet in other embodiments decision 910 may be performed after block 908 has been initiated.

In one embodiment, a negative finding at decision 910 may remove or negate the "running" classification initially provided to the data at block 902 (see, e.g., block 912). Further embodiments, however, may utilize data regardless of whether that data is considered to be indicative of running or walking (or other activity classification). In one embodiment, data may be utilized in systems and methods for determining energy expenditure. Systems and methods for determining energy expenditure may utilize this (and other) data to categorize the sensed data into an activity. Such examples are explained later in this disclosure.

Returning to decision 910, if the threshold is met (or if the requirement for a threshold is absent), block 914 may be implemented to place the activity into a classification buffer. The classification buffer may be filled with the walking data for which speed was determined (from block 906) as well as the running data from block 908 and 910. In certain embodiments, the activity (e.g., walking or running), the activity time duration, and calculated speed are placed in the classification buffer. In one embodiment, an activity buffer may be about 12.8 seconds in duration. Yet other durations are within the scope of this disclosure. As discussed above, any buffer (such as the classification buffer) may have a different duration than another buffer (such as the analysis or sample buffer), however, there is no requirement that these (or other) buffers are distinct buffers; rather the second buffer may be a collection of several first buffers and or a logical extension of other buffers. In this regard, collected data may be stored in a single location but utilized (even simultaneously for two different buffers, processes, and/or analyses).

Decision 916 may be implemented to determine if the classification buffer of block 914 is full. In one embodiment, the determination may be based upon or correlated to a duration of activity data, such as 12.8 seconds in one embodiment. The analysis buffer may be deemed full upon comprising a quantity of samples. In one embodiment, the analysis buffer may comprise 12 samples.

As discussed above, flowchart 900 provides one of many embodiments that may be executed in accordance with this disclosure. For example, system 100 may process data received from one or more of the sensors described above to attempt to classify a user's activity. For example, system 100 may compare a sensor signal to one or more signal or activity "templates" or "signatures" corresponding to selected activities. In certain embodiments, templates may be created by attaching sensors to a user and monitoring signals generated when the user performs various activities. In accordance with certain embodiments, an activity may be associated with an activity template specific to user 124. In one such embodiment, user 124 may be assigned a default template for a specific activity unless a specific template has been assigned to that activity. Thus, user 124 may create or receive (but is not required to create or receive) an activity template that may be more accurate than a default template because the template is more specific to the user and/or the activity. User 124 may have the option to create templates for one or more predefined or undefined activities. A specific or otherwise new template might be shared among the community of users. Shared templates may be based on a variety of different sensors. In some embodiments templates may be refined or adjusted for use with different sensors. For example, a template that was created for use with a shoe based sensor may be refined for use with a wrist-worn sensor.

An activity template may be created from data obtained from one or more of a plurality of different sensors. For example, a first group of sensors (e.g. sensors 126 and 138) may be utilized in the formation or refinement of a first activity template; however, a second group of sensors (e.g., sensors 128 and 140) may be utilized in the formation or refinement of a second activity template. In yet further embodiments, a third group of sensors, such as sensors 128 and 140 (and/or other sensors), may be utilized in the creation of the first activity template for a second user (e.g., not user 124) than utilized for the formation of the same activity template as user 124. Thus, in accordance with certain embodiments, there is no requirement that data from a specific sensor be received for either: 1) the same activity template for different users; and/or 2) different activity templates for the same user.

In one embodiment, a wrist mounted accelerometer, which may be a multi-axis accelerometer, may be attached to a user and signal templates based on the accelerometer output when the user runs, walks, etc. may be created. The templates may be functions of the sensor(s) used and/or the locations of the sensor(s). In some embodiments, a single signal (or value) is created by combining multiple signals (or values). For example, three outputs of a three axis accelerometer may be summed or otherwise combined to create one or more signals. Example step 902 may include comparing a signal, multiple signals or a combination of signals to one or more templates. In some embodiments, a best match approach may be implemented in which every activity is attempted to be classified. In other embodiments, if a signal, multiple signals or combination of signals does not sufficiently match a template, the activity may remain unclassified.

FIG. 10 shows a flowchart 1000 of yet another embodiment for estimating energy expenditure. In one embodiment, motion data from one or more sensors may be obtained. (see, e.g., block 1002). In certain implementations, sensor data from only a single device configured to be attached to a human appendage may be obtained. In one embodiment, sensor data from a single accelerometer (single axis or multiple axis) may be used alone. In one embodiment, raw sensor data may be used. In one embodiment, raw acceleration data may be obtained. The sensor data may be processed to remove the effects of gravity. In one embodiment, the Euclidean norm of the sensor data (raw or processed) may be calculated. The data may comprise of consist of accelerometer data. Accelerometer data may be obtained at 25 Hz. In certain embodiments, a sample buffer comprising 25 samples is obtained. In one embodiment, each sample represents about 0.5 seconds of activity data.

Block 1004 may be implemented to classify the data (or attempt to classify data) into an activity. This may occur once a buffer, such as a sample buffer, is full. For example, obtaining 25 samples in a 25 sample buffer. The classification of activity may include one or more of the classification systems or methods described herein, including one or more aspects described in relation to FIG. 9. In one embodiment, Fourier transform step algorithm may be implemented, such as described previously in this disclosure. Of course, the data may already be classified or readily classified based upon previous classification of derivative data. Thus, in one embodiment, corresponding activity classifications may already be known for at least a portion of the data. In certain embodiments, activity may be classified as walking, jogging, running, (or unclassified). In another embodiment, data may be classified as either walking or running (or deemed unclassified).

An energy expenditure value may be determined for the classified activity (see, e.g., block 1006). The determination of the energy expenditure value may utilize one or more data points comprising the user's personal information, such as for example, age, weight, sex, height, and combinations thereof. Yet in other embodiments, some or all of any known personal information may not be utilized. In one embodiment, the user information may be stored on a non-transitory computer-readable medium located on the device comprising a sensor that sensed activity data utilized in the analysis. In one embodiment, the user information is obtained entirely from a device configured to be worn on a human appendage that comprises at least one sensor. In one embodiment, the device contains all of the sensors and user information utilized in the determination.

In yet other embodiments, however, system and methods could calculate energy expenditure values without at least one type of personal information based upon whether the data is obtained from a first sensor (or first type of sensor). In other embodiments, at least one type of personal information may be utilized if data is obtained from a second sensor (or type of sensor). Sensors or devices may be identifiable from a unique identifier, such as for example, a serial number, MAC address, or the like. Yet in other embodiments, a sensor or device may be identifiable from a non-unique identifier, such as for example, a model number from a device with a sensor. In further embodiments, a default value may be obtained or derived. In certain embodiments, a default value may be intentionally discounted due to variations from device to device.

Systems and methods may be implemented to assign an energy expenditure value for unclassified data (see, e.g., block 1008). In one embodiment, a Euclidean mean value may be calculated based upon the data. For example, the average acceleration of the Euclidean norm may be calculated. In one embodiment, if the entire (or substantially the entire) duration of activity data reflects that the activity was consistent, such as for example, 1 second intervals within the duration indicated the user was walking or conducting a consistent activity, then a first default process may be utilized to determining activity. Data from one or more sensors may be utilized. In one such embodiment, data from several accelerometers (and/or a multi-axis accelerometer) may be normalized to generate a value. Values (which may be normalized) may be placed into a buffer. In one embodiment, a sample buffer may be utilized. The sample buffer may be a 1-second buffer. In certain embodiments, a variable sampling rate may be utilized. In one such embodiment, 25 samples may be obtained in 1 second. In yet other embodiments, other rates may be utilized, including for example, a fixed rate. In one embodiment, data from several accelerometers (and/or a multi-axis accelerometer) captured at an interval (e.g., 1 second) may be summed and the average of the absolute value of the acceleration may be calculated. A default energy expenditure value may be assigned based upon the acceleration count. An equivalence value, such as a Metabolic Equivalence Value (MET value) may be determined from the data within the buffer. In one embodiment, a rectangular hyperbola process may be utilized in determinations of an equivalence value.

In certain embodiments, the determination of the energy expenditure value may utilize one or more data points comprising the user's personal information, such as for example, age, weight, sex, height, resting metabolic rate (RMR) and combinations thereof. Yet in other embodiments, some or all of any known personal information may not be utilized. In one embodiment, the user information may be stored on a non-transitory computer-readable medium located on the device comprising a sensor that sensed activity data utilized in the analysis. In one embodiment, the user information is obtained entirely from a device configured to be worn on a human appendage that comprises at least one sensor. In one embodiment, the device contains all of the sensors and user information utilized in the determination. The energy expenditure value may be determined for each 1 second interval of data based on the user's RMR and a MET value.

In certain embodiments, the energy expenditure of the classified and/or unclassified energy expenditure values may be accumulated (see, e.g., block 1010). Energy expenditure values for both the classified and the unclassified activities may be accumulated, and in one embodiment, caloric burn may be determined using this and/or other information. In accordance with one implementation, the energy expenditure values for the classified activity may be placed in a buffer, which in one embodiment may be a buffer having a time frame that is larger than an activity buffer or another buffer. (see, e.g., sub-block 1010*a*). This, in certain embodiments, may ensure that the information, such as that from the 12.8 activity buffer (See, block 910), is not double counted. Sub-block 1010*b* may be adjusted by subtracting the previous 12.8 second and adding the energy expenditure (e.g. caloric burn) from the classified activity. Those skilled in the art will appreciate that 13 second and 12.8 seconds are merely examples. In certain embodiment, the buffer may be a first in-first out (FIFO) buffer. The total energy expenditure points for both the classified and the unclassified activities may then be totaled for the respective time period and one or more buffers (such as the sample, energy expenditure, and/or activity buffer(s)) may be reset.

FIG. 11 shows a visual depiction of an example correlation of activity to energy expenditure determinations. In one embodiment, the depiction shows an example correlation of acceleration measurements that is not classified (such as part of the flowchart shown as FIG. 10) correlated to energy expenditure values. Yet in other embodiments, at least a portion of classified data may be correlated through this or similar processes. The top portion of FIG. 11 includes graph 1100 that plots measured acceleration (see, y-axis 1102) over time (see, x-axis 1104). In one embodiment, the acceleration may be analyzed as the Euclidean normal of multiple axis (such as the x, y and z axes) over time. Data section 1106 shows a collection of data (namely between 0.3 to about 0.5 on the x-axis 1104), in which the acceleration values are consistently elevated when compared to other values on graph 1100, such as the acceleration values of data section 1108 which correspond to around 0.9 on the x-axis 1104. Specifically, the acceleration data values of data section 1108 are around zero (0). As seen in graph 1110, located on the lower portion of FIG. 11, the cumulative energy expenditure (as measured in calories along the y-axis (1112) along the same time scale (see, scale 1114 being at about the same scale as x-axis 1104). As further seen in graph 1110, the corresponding energy expenditure is correlated to the acceleration values set forth in graph 1100. Thus, the corresponding accumulation at about location 1116 (which corresponds to data section 1106) is much higher than the corresponding accumulation of energy expenditure values at about location 1118, which corresponds to data section 1108). In fact, location 1118 shows little or no increase in energy accumulation values.

III. Energy Expenditure Point Calculations

In some embodiments there is not a one-to-one correlation between an activity and an activity factor. The selection of an activity factor may be based on several different variables, such as the activity identified, steps taken, heart rate, and intensity of a workout. The actual activity identified may correspond to a group of activity factors and the other variables may be used to make a final selection of an activity factor. In still other embodiments there is a one-to-one correspondence between an activity and an activity factor. In some of these embodiments, other variables such as steps taken, heart rate, and intensity of a workout may be used to adjust or compensate for the activity factor. Of course, in some embodiments there is a one-to-one correlation between activities and activity factors and no adjustments or compensations are made to the activity factor.

FIG. 12 illustrates a method for calculating energy expenditure values, such as points, in accordance with an embodiment of the invention. After at least one of user's 124 activity is classified (see, e.g., block 1204, which may use for example one or more classification systems and methods disclosed herein), block 1204 may be implemented to determine a corresponding activity factor. An activity factor may correspond to brisk running, running at a moderate pace, walking slowly or any other activity. An activity factor for an activity may be related to calories or energy generally required to perform the activity. If an activity was not classified in step 1202, a default activity factor may be selected or derived. In some embodiments multiple default activity factors may be utilized. An activity's intensity, duration or other characteristic(s) may be assessed, from which one or more default activity factors may be applied. The plural activity factors may be set via medians/averages, ranges, or other statistical approaches.

In various embodiments of the invention, activity factors are used to calculate energy expenditure points. After at least one of user's 124 activity is classified, in step 1206 energy expenditure points ("EEP") may be calculated. The use of energy expenditure points allows for comparison of activity levels and may promote collaboration among users, normalize for competition among users of different capabilities, and otherwise encourage activity. In one embodiment, energy expenditure points are calculated as follows:

$$EEPs = AF * duration \quad \text{(Equation 1)}$$

Wherein:
EEPs=energy expenditure points
AF=activity factor determined in step 1204
duration=duration of the activity classified in step 1202

Step 1206 may be performed at a device that includes sensors that monitor activity and/or at another device that includes a processor, such as a mobile phone (see, e.g., 138) or server (see, e.g., 134). In yet other embodiments, block 1206 may be performed at a device configured to be worn on a human appendage (e.g., wrist, arm, neck, ankles, leg, etc.). The device may be the same device comprising sensors utilized to collect the activity data. In one embodiment, the same device comprises sensors that collect all of the sensor data and/or otherwise contains all the information locally to compute the activity data.

In some embodiments, Equation 1 may be modified to include a scalar that is multiplied by the activity factor and duration. The scalar may be selected so that typical energy expenditure points fall within a desired range. The range of points may be desired for various games or competitions.

Variations of Equation 1 may be used in other embodiments of the invention. In some embodiments, users may select an equation and/or one or more variables, such as for example, a scalar. Equations may be selected for different games and competitions. In one example a group may set handicaps among the players based on fitness, so that the most fit generate EEPs only if they do a common activity or set of activities for longer period(s) of time. A group of users participating in an energy expenditure point competition may agree on a particular equation or method before beginning the competition. In some embodiments of the invention, a user may participate in multiple competitions and earn different points for the same activity because of different calculation methods. For example, a user may be participating in two competitions that have unique calculation methods. The user may earn two different point totals for the two different games and a third point total foe their overall energy expenditure. Some point totals may be maintained separate from an overall point total.

After the energy expenditure points are calculated, the calculated points may be combined, such as being added, to a total in block 1208. The total may allow user 124 (and/or selected individuals or groups approved by user 124) to see how many points are earned over various periods of time, such as days, weeks and months. Totals may also be calculated for multiple time periods. For example, a user may receive totals for periods that include 24 hours, one week, one month and one year. In some embodiments users may select other time periods or deselect time periods. A user may track multiple time periods concurrently and track points award since the beginning of use of a device or start of a program. The total for any giving time period may represent points earned for several activities. For example, in a day a user may receive points for walking, jogging and sprinting during different time periods. As mentioned above, the points earned for each activity may be a function of a corresponding activity factor.

Energy expenditure points may be deducted when user 124 has been inactive for a predetermined period of time or enhanced when certain criteria are met. This feature may be included with all calculations or may be used in various games and competitions. For example, in step 1214 it may be determined whether an adjustment criterion has been met. The adjustment criteria may include inactivity for a predetermined time period. In some embodiments inactivity is not determined by merely determining that an amount of time has passed since with user was active.

When an adjustment criterion has been met, the total of energy expenditure points may be adjusted in step 1210. The adjustment may be a function of duration of inactivity. In some embodiments, a device may warn user 124 (or authorized groups/individuals) that they are close to receiving a reduction in energy expenditure points to encourage activity. It yet other embodiments, an alarm may notify user 124 (and/or other authorized individuals and/or groups) that they have received a reduction of energy expenditure points. In certain embodiments, team-mates and/or competing users may be notified of a reduction (or potential for reduction). In further embodiments, teachers, trainers, and/or parents may more readily monitor the physical activity of others. When a user has not been inactive, the process may end in step 1214. Of course, the method shown in FIG. 12 may be repeated at various intervals and allow for tracking points concurrently for different time periods, such as days, weeks and years.

In another aspect, a device 10, such as device 226 may provide a message based on inactivity or non-active periods. If the device senses that the user has been in a non-active (e.g., low activity) state for a predetermined amount of time, an alert message may be delivered to the indicator system or display to remind the user to become more active. The alert message can be delivered in any of the manners described herein. The threshold levels of a low activity state and amount of inactive time could also vary and be individually set by the user.

In some arrangements, user non-activity or inactivity may also be detected and affect the user's progress toward completion of an activity goal. For example, inactivity may be detected when a user does not exhibit movement of a particular level or a type of movement for a specified amount of time, does not exhibit a heart rate of at least a threshold level, does not move a sufficient amount of distance over an amount of time and the like and/or combinations thereof. For arrangements in which a user accumulates activity points to reach an activity point goal, points or a value may be deducted from the user's activity point or other activity metric total when an amount of non-activity (e.g., inactivity or sedentary state) is detected. Various conversion rates for converting inactivity to activity point deductions may be used. In a particular example, 10 minutes of inactivity may correspond to a 5 point deduction. In another example, 30 minutes of inactivity may correspond to a 100 point deduction. Loss or deduction of activity points may be linear or may be non-linear, for example, exponential, parabolic and the like.

A user's non-active time may include inactive time and sedentary time. Inactivity and sedentary time may be defined by different movement, heart-rate, step or other thresholds or may be defined using the same thresholds. In one example, sedentary time may have a higher threshold (e.g., requiring a higher level of activity) than an inactivity threshold. That is, an individual may be considered sedentary but not inactive. The non-active threshold may correspond to the sedentary threshold or a higher threshold, if desired. Alternatively, an inactivity threshold may be greater than a sedentary threshold. There may also be multiple sedentary thresholds, inactivity thresholds and/or non-active thresholds (e.g., each of the sedentary and inactivity thresholds may be a non-active threshold). Different point deductions or rates of point deductions may also be defined between the multiple thresholds and levels of little to no activity (e.g., non-activity). For example, a user may lose 50 points per hour for inactivity and 30 points per hour for sedentary activity or vice versa. Further, activity point deduction may be triggered at different times depending on if the user is inactive or sedentary. For instance, a user may begin losing activity points after 30 minutes of inactivity or 45 minutes of being sedentary. Additional thresholds (e.g., more than two thresholds) and corresponding rates of activity point loss may also be defined.

In some arrangements, various sensors may be used to detect non-active periods of time. As discussed, non-activity time periods may be defined based on heart-rate, amplitude of a movement signal, step rate (e.g., <10 steps per minute), or the like. Alternatively or additionally, inactivity and sedentary time periods may be measured based on a physical position, body position, body orientation, body posture of or type of activity being performed by the individual. The detrimental effects of various physical inactivity or sedentary body positions or orientations may also differ. Accordingly, 30 minutes of reclining may introduce the same health risks as 45 minutes of sitting. The potential for health risks may also be time-dependent. Accordingly, non-activity (e.g., sleeping) for a specified range of durations and during a specified range of time might not introduce health risks. In one example, sleeping for 7-9 hours between 9 PM and 9 AM might not introduce detrimental health risks and thus, might not contribute to activity point or other activity metric value deduction. Indeed, in some example, a lack of inactivity (such as sleep) for a specified range of durations and/or during a specified range of time may be considered detrimental to a user's health. Thus, activity points may be deducted or activity points may be accumulated at a slower rate during these times.

Alternatively or additionally, the amount by which a value of the activity metric (e.g., an activity points) is decreased may be determined based on time of day, location of the user, physical position of the user, level of inactivity and the like. For example, a user may lose greater value in an activity metric and/or at a faster rate during the afternoon than during the evenings. In another example, if a user is at a gym, the user may lose fewer activity points or other activity metric or lose value in the metric at a slower rate than if the user was located at home.

To account for the variances in types of non-active activity (e.g., below a requisite level of movement to be considered activity), a system may distinguish between physical body positions or orientations including, for example, sleeping, reclining, sitting and standing. Distinguishing between different physical body positions and orientations may include placing sensors at different locations of the user's body to detect the individual positions of each body part. The physical body position of the user may then be determined based on the relative positions of the body parts to one another. For example, when a knee location sensor is within a first threshold distance of a waist or chest sensor, the system may determine that the user is sitting. If the knee location sensor is outside of the first threshold distance, the system may determine that the user is standing. In the above example, the system may use a portion of the distance such as the vertical distance. By using vertical distance alone or in combination with an absolute distance (e.g., straight line distance between the two sensors), the system may further distinguish between when a user is lying down and standing up. For example, a lying down position may correspond to a very low vertical distance between the knee sensor and chest or waist sensor even though the absolute distance may be larger. A standing position may correspond to a larger vertical distance between the knee sensor and the waist or chest sensor but exhibit a similar absolute distance. In other examples, an angle formed by the various sensors may be used to determine an individual's position. Additionally or alternatively, the location of the user's various body parts may be evaluated in conjunction with accelerometer or movement data to determine if the user is exhibiting movement or (e.g., at, above or below) a specified level of movement.

In addition to deductions in activity points, the system may alert a user to inactivity to encourage active lifestyles. In one example, the system may alert the user by displaying a message or indicator on a device such as the wearable device assembly described herein after a specified amount of inactivity such as 2 minutes, 5 minutes, 30 minutes, 1 hour and the like. The amount of inactivity time may be additive over non-consecutive time periods. An amount of consecutive inactivity time may alternatively or additionally be tracked. For example, if the user is inactive between 10:15 and 11:00 AM and then again between 2:00 and 2:30 PM, the total amount of non-active time may be 1 hour and 15 minutes. The message or indicator of inactivity may be provided as a warning prior to deducting activity points. For example, the message may indicate that X amount of activity points will be deducted if the user does not exhibit a sufficient level of activity within a specified amount of time (e.g., 30 minutes, 5 minutes, 10 seconds, 30 seconds, 1 hour, 2 hours, etc.). Accordingly, the device may include a non-active timer to determine the amount of user non-activity. Additionally, the message may provide a suggestion as to a type of activity the user should perform to counter any risks introduced by the inactivity. For example, the system may suggest that the user walk 1 hour at a 10 minute mile pace. When the user has counteracted or accounted for the risks or negative effects of the detected amount of inactivity time, a celebratory message or other indication may be provided.

Warnings, point deductions and/or other notifications may be provided if a user returns to a sedentary or a non-active mode within a specified amount of time of exiting sedentary or a non-active mode. For example, the user may exercise or exhibit a sufficient level of activity to exit the sedentary or a non-active mode for a period of 10 minutes. However, the system or device may require at least 30 minutes of activity to avoid additional warnings for a period of time such as 1 hour, 2 hours, 3 hours, etc. For example, the warnings may indicate that the user did not exhibit activity for a sufficient amount of time or a sufficient level of activity or a combination thereof. Additionally, multiple sedentary periods within short amounts of time (e.g., a threshold amount of time) may require higher or additional levels of activity to counteract potential sedentary effects including health risks and the like. In a particular example, the user may be required to perform a higher level of activity to halt point deduction.

The device or other system may further advise a user as to an amount of non-active time allowed before negative health effects may occur. In one example, the device or system may include a countdown indicating a remaining amount of allowable non-active time before potential health risks may begin taking effect. An amount of permissible non-active time may be earned or accumulated based on an amount of activity performed. Accordingly, the device may also provide suggestions or recommendations as to a type and/or duration of activity that may be performed to earn a specified amount of non-active time (e.g., 1 hour of TV watching). Different types of non-active or sedentary activities may require different types or amounts of activity. For example, 1 hour of reclining may require more strenuous or longer exercise than 1 hour of sitting. In another example, 1 hour of sitting while knitting may require less strenuous or a lower amount of exercise or activity than 1 hour of sitting while watching television. According to one or more arrangements, recommendations may be generated based on empirical data and/or predefined programming and data tables specifying a type and/or duration of activity and a corresponding amount of permissible non-activity.

The device or activity tracking system may further recommend activities based on historical records. For instance, the device or tracking system may determine activity performed by the user in the past and generate recommendations based on those types of activities. Additionally or alternatively, the device or tracking system may generate recommendations for specific workouts performed by the user in the past. For example, a user may need to perform 500 calories worth of activity to counteract 2 hours of TV watching. In such a case, the system may recommend a particular workout performed by the user in the past in which the user burned 500 calories. Combinations of historical activity types and specific historical workouts may be used to generate recommendations. In one example, the system may recommend one of two workouts that the user has performed in the past based on a type of workout that the user appears to prefer. The preference may be determined based on a number of times the user has performed each type of workout. A workout or activity type may also be recommended based on location and time. For example, if a user previously performs a particular type of activity or a particular workout routine at the same location and/or at the same time, the system may recommend that type of activity or workout routine. Other recommendations algorithms and factors may be used.

System 100 may be configured to transmit energy expenditure points to a social networking website. The users may be ranked based on their total number of points for a desired time interval (e.g., rank by day, week, month, year, etc.).

CONCLUSION

Providing an activity environment having one or more of the features described herein may provide a user with an experience that will encourage and motivate the user to engage in athletic activities and improve his or her fitness. Users may further communicate through social communities and challenge one another to participate in point challenges.

Aspects of the embodiments have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

We claim:

1. A unitary apparatus comprising:
  a housing configured to be worn on an appendage of a user, comprising:
    a processor;
    a sensor configured to capture motion data of the user;
    a non-transitory computer-readable medium comprising computer-executable instructions that when executed by the processor perform at least:
      capturing motion data of the user with the sensor while being worn on an appendage of the user;
      detecting appendage swings peaks and bounce peaks in the motion data;
      calculating a step frequency of the user during a time period based on at least one of appendage swing peaks or bounce peaks in the motion data;
      classifying the motion data based upon the calculated step frequency during the time period;
      calculating an energy expenditure value for the user, based on the classified motion data; and
      calculating an energy expenditure points value, based on the calculated energy expenditure value.

2. The unitary apparatus of claim 1, wherein the non-transitory computer-readable medium of the unitary apparatus comprises further instructions that when executed by the processor, perform at least:

receiving a metabolic equivalence value corresponding to the classified data from the computer-readable medium on the unitary apparatus, wherein the metabolic equivalence value is utilized to calculate the energy expenditure value.

3. The unitary apparatus of claim 2, wherein the non-transitory computer-readable medium of the unitary apparatus comprises further instructions that when executed by the processor, perform at least:

determining that at least a portion of the motion data cannot be categorized as either running or walking, and in response, conducting an energy expenditure determination that assigns a metabolic equivalence value to the uncategorized motion data.

4. The unitary apparatus of claim 3, wherein the calculation of the energy expenditure value comprises combining energy expenditure values of classified activities and energy expenditure values of unclassified activities.

5. The unitary apparatus of claim 2, wherein the time period is a first time period, and further comprising a display configured to be observable by the user while being worn by the user, and the non-transitory computer-readable medium of the unitary apparatus comprises further instructions that when executed by the processor, perform at least:

combining the energy expenditure value for the first time period with an energy expenditure value from a second time period to determine an accumulated energy expenditure value; and displaying the accumulated energy expenditure value on the display of the unitary apparatus.

6. The unitary apparatus of claim 1, wherein the sensor comprises an accelerometer, and the non-transitory computer-readable medium of the unitary apparatus comprises further instructions that when executed by the processor, perform at least:

determining accelerometer magnitude vectors from the accelerometer for a time frame;

calculating an average value from magnitude vectors for the time frame; and determining whether the magnitude vectors for the time frame meet an acceleration threshold and be used to quantify steps for at least the time frame.

7. The unitary apparatus of claim 6, wherein the non-transitory computer-readable medium of the unitary apparatus comprises further instructions that when executed by the processor, perform at least:

determining that the magnitude vectors for the time frame did not meet an acceleration threshold and therefore are not used to quantify steps for at least the time frame; and utilizing the data that did not meet the acceleration threshold in a calculation of an energy expenditure value.

8. The unitary apparatus of claim 7, wherein the non-transitory computer-readable medium of the unitary apparatus comprises further instructions that when executed by the processor, perform at least:

determining that at least a portion of the data meets the acceleration threshold and in response, placing acceleration data within an analysis buffer;

calculating a mean acceleration value of the analysis buffer to create a search range of acceleration frequencies related to an expected activity;

analyzing frequencies of the acceleration data within the search range to identify at least one bounce peak and one appendage swing peak; and determining whether to utilize at least one of the bounce peak and the appendage swing peak to quantify steps.

9. The unitary apparatus of claim 8, wherein the search range comprises an appendage swing range and a bounce range, and wherein analyzing frequencies within the acceleration data comprises:

identifying a first frequency peak as an appendage swing peak if the first frequency peak is within the appendage swing range and meets an appendage swing peak threshold; and identifying a second frequency peak as a bounce peak if the second frequency peak is within the bounce range and meets a bounce peak threshold.

10. The unitary apparatus of claim 9, wherein the determining whether to utilize the bounce peak or the appendage swing peak to quantify steps comprises:

quantifying a number of appendage swing peaks and bounce peaks; and utilizing the quantification of appendage swing peaks and bounce peaks in a calculation to choose a step frequency and step magnitude.

11. The unitary apparatus of claim 10, wherein the non-transitory computer-readable medium of the unitary apparatus comprises further instructions that when executed by the processor, perform at least:

based upon the chosen frequency and step magnitude, quantifying a number of steps taken by the user during a respective time frame; and based upon the number of steps taken, classifying the user's motion as running or walking for the respective time frame.

12. The unitary apparatus of claim 11, wherein the time period is a first time period, and the non-transitory computer-readable medium of the unitary apparatus comprises further instructions that when executed by the processor, perform at least:

based on the classified user's motion, assigning an energy expenditure value for the first time period;

combining the energy expenditure value for the first time period with an energy expenditure value from a second time period to calculate an accumulated energy expenditure value; and displaying the accumulated energy expenditure value on the display of the unitary apparatus.

13. The unitary apparatus of claim 12, wherein the energy expenditure value from the second time period comprises data that is not classified into an activity.

14. The unitary apparatus of claim 12, wherein the non-transitory computer-readable medium of the unitary apparatus comprises further instructions that when executed by the processor, perform at least:

receiving a user input from a user input device located on the user input device, and in response, displaying the energy expenditure value on the display.

15. A non-transitory computer-readable medium comprising computer-executable instructions that when executed by a processor perform at least:

capturing motion data of a user with a sensor worn on an appendage of the user;

quantifying steps taken by the user, comprising:

detecting appendage swing instances and bounce instances in the motion data from the sensor worn on the appendage;

using only motion data collected from the sensor worn on the appendage, calculating a step frequency of the user during a time period based on at least one of the utilized appendage swing instances or bounce instances in the motion data;

calculating an energy expenditure value for the user, based on the calculated step frequency; and calculating an energy expenditure points value, based on the calculated energy expenditure value.

16. The non-transitory computer-readable medium of claim 15, wherein the computer-executable instructions, when executed by the processor, are further configured to perform at least:

generate a warning message for the user prior to adjust the energy expenditure points value.

17. The non-transitory computer-readable medium of claim 16, wherein the time period is a first time period, and wherein the calculated energy expenditure value is a first energy expenditure value and the computer-readable medium further comprising instructions that when executed by the processor, perform at least:

combining the energy expenditure value for the first time period with an energy expenditure value from a second time period to determine an accumulated energy expenditure value; and displaying the accumulated energy expenditure value on a display of a device configured to be worn by the user during collection of the motion data.

18. The non-transitory computer-readable medium of claim 17, wherein captured motion data of the user is only from one or more sensors that are located on the device.

19. The non-transitory computer-readable medium of claim 18, wherein all information used to calculate the energy expenditure value is either (a) located on the device before collection of the motion data or (b) derived from the motion data without information external to the device.

20. The non-transitory computer-readable medium of claim 19, wherein the sensor comprises an accelerometer.

* * * * *